(12) United States Patent
Koda et al.

(10) Patent No.: US 11,398,109 B2
(45) Date of Patent: *Jul. 26, 2022

(54) FINGERPRINT READING DEVICE AND FINGERPRINT READING METHOD

(71) Applicant: NEC CORPORATION, Tokyo (JP)

(72) Inventors: Yoshinori Koda, Tokyo (JP); Teruyuki Higuchi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/085,001

(22) Filed: Oct. 30, 2020

(65) Prior Publication Data

US 2021/0049337 A1    Feb. 18, 2021

Related U.S. Application Data

(63) Continuation of application No. 16/313,743, filed as application No. PCT/JP2018/027400 on Jul. 20, 2018, now Pat. No. 10,860,833.

(30) Foreign Application Priority Data

Jul. 26, 2017  (JP) .................................. 2017-144532

(51) Int. Cl.
*G06V 40/13*  (2022.01)
*G06V 40/12*  (2022.01)

(52) U.S. Cl.
CPC ...... *G06V 40/1318* (2022.01); *G06V 40/1329* (2022.01); *G06V 40/1335* (2022.01); *G06V 40/1341* (2022.01)

(58) Field of Classification Search
None
See application file for complete search history.

(56) References Cited

U.S. PATENT DOCUMENTS 6,011,860 A    1/2000  Fujieda et al.
6,668,071 B1  12/2003  Minkin
(Continued)

FOREIGN PATENT DOCUMENTS

CN      102292740 B    1/2014
EP       2511872 A1   10/2012
(Continued)

OTHER PUBLICATIONS

Written Opinion for PCT/JP2018/027400 dated Aug. 21, 2018 [PCT/ISA/237].

(Continued)

*Primary Examiner* — Joseph R Haley
(74) *Attorney, Agent, or Firm* — Sughrue Mion, PLLC

(57) ABSTRACT

Provided are a fingerprint reading device and a fingerprint reading method that can appropriately read a fingerprint even when reading a fingerprint of a relatively soft finger that may be easily subjected to significant elastic deformation. The fingerprint reading device includes: a placement portion on which a finger is placed, provided with a reading face so as to be able to move between first and second positions; a drive unit that causes the reading face to move between the first and second positions; and a reading unit that reads a fingerprint when the reading face is positioned at the first position, the drive unit causes the reading face to move to the second position and further move from the second position to the first position, and the reading unit reads a fingerprint when the reading face has moved from the second position to the first position.

20 Claims, 23 Drawing Sheets

(56) References Cited

U.S. PATENT DOCUMENTS

| | | | |
|---|---|---|---|
| 6,912,299 B1 | 6/2005 | Hoshino | |
| 7,245,745 B2 * | 7/2007 | Nagasaka | G06K 9/00 |
| | | | 382/115 |
| 2011/0063430 A1 | 3/2011 | Hyun | |
| 2011/0260966 A1 | 10/2011 | Okazaki | |
| 2012/0212322 A1 * | 8/2012 | Idsoe | G07C 9/00944 |
| | | | 340/5.53 |
| 2018/0260603 A1 | 9/2018 | Aronoff | |
| 2018/0342052 A1 | 11/2018 | Higuchi et al. | |
| 2019/0087632 A1 | 3/2019 | Raguin | |

FOREIGN PATENT DOCUMENTS

| | | |
|---|---|---|
| JP | S64-68894 A | 3/1989 |
| JP | H06-60170 A | 3/1994 |
| JP | 10-289304 A | 10/1998 |
| JP | 11-225998 A | 8/1999 |
| JP | 2003-044857 A | 2/2003 |
| JP | 2003-070769 A | 3/2003 |
| JP | 2005-160846 A | 6/2005 |
| JP | 2005-182474 A | 7/2005 |
| JP | 2010-092508 A | 4/2010 |
| WO | 2010/086970 A1 | 8/2010 |
| WO | 2011070886 A1 | 6/2011 |
| WO | 2017/047090 A1 | 3/2017 |
| WO | 2017/047091 A1 | 3/2017 |
| WO | 2017/047092 A1 | 3/2017 |

OTHER PUBLICATIONS

Communication dated November 4, 2019 from the European Patent Office in application No. 18814764.9.
International Search Report for PCT/JP2018/027400 dated Aug. 21, 2018 [PCT/ISA/210].
Communication dated Oct. 13, 2020 by the Japanese Patent Office in application No. 2019-532576.
Japanese Office Action for JP Application No. 2020-188398 dated Nov. 9, 2021 with English Translation.
Indian Office Action for IN Application No. 201917053508 dated Aug. 10, 2021.

* cited by examiner

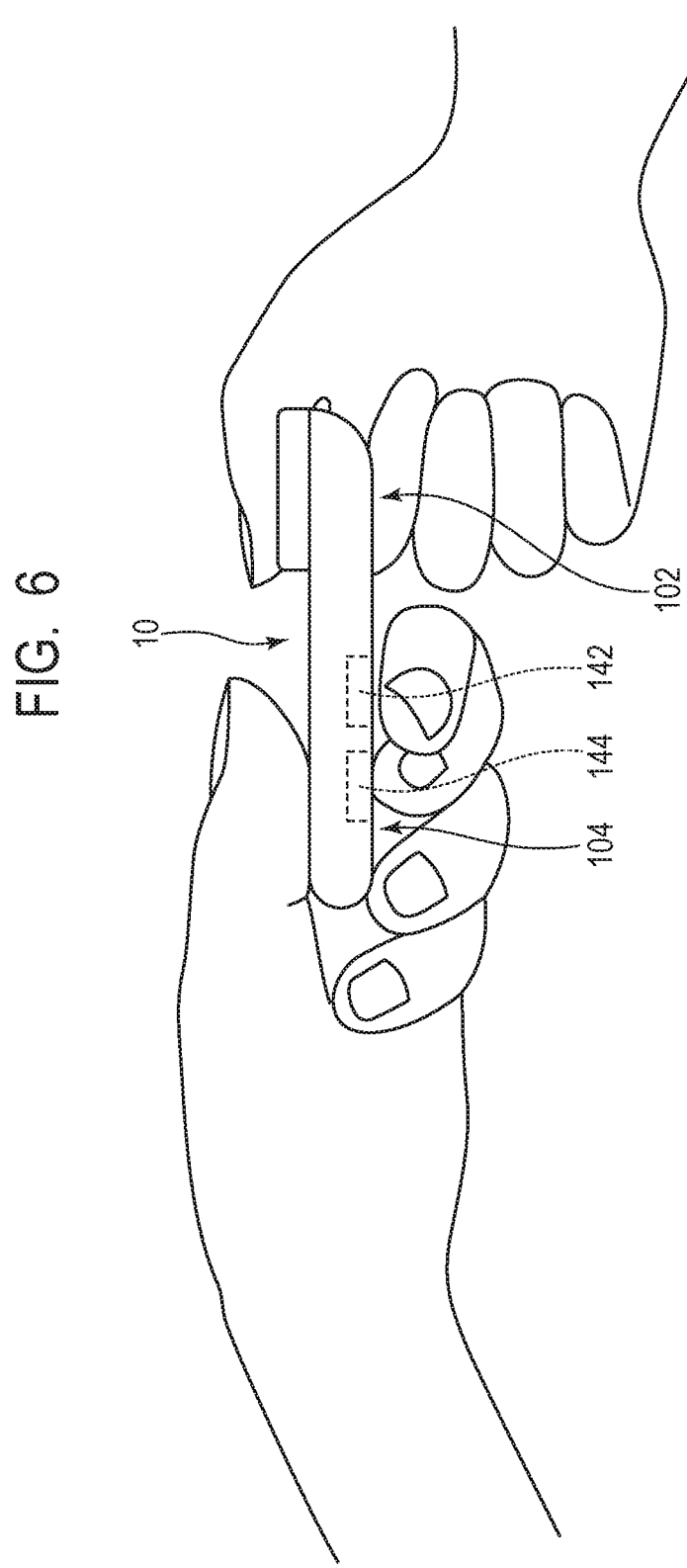

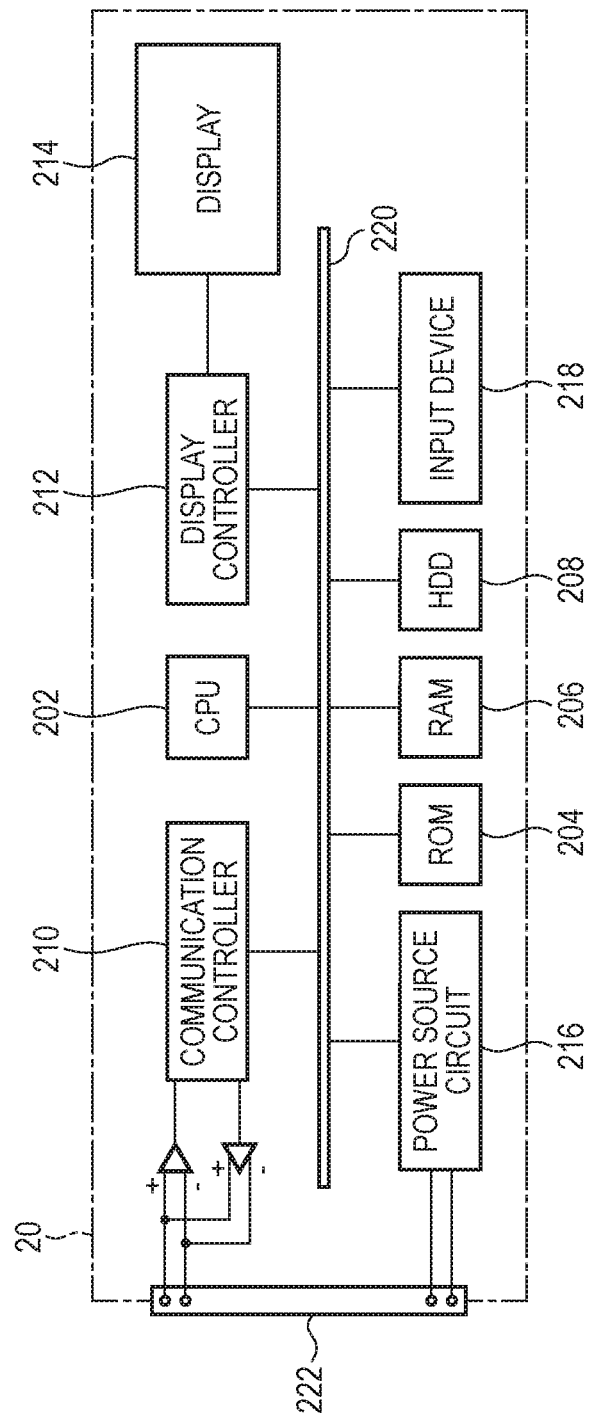

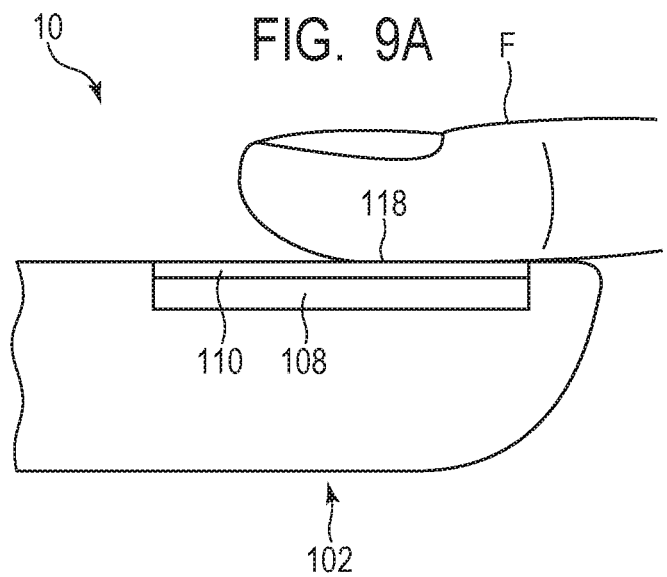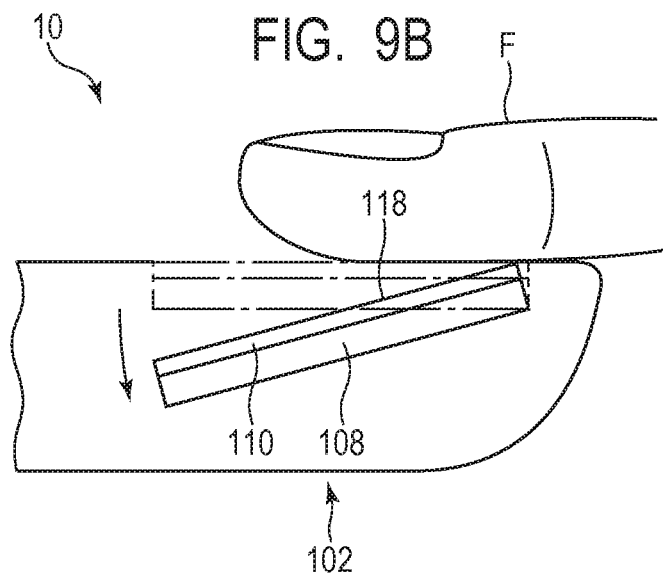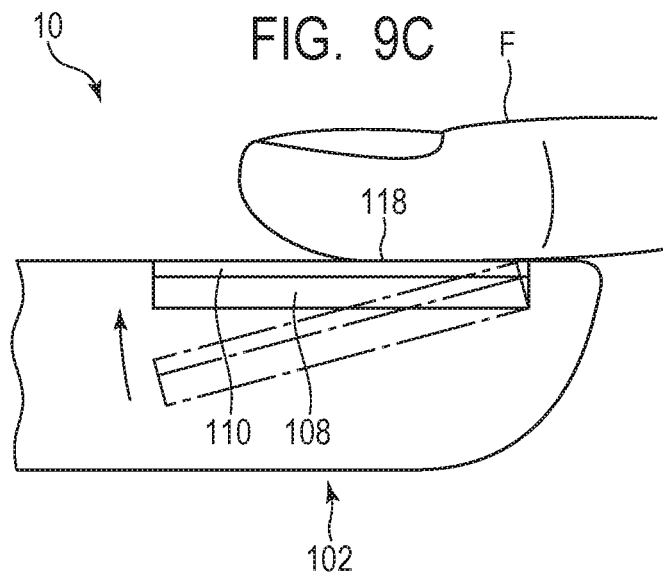

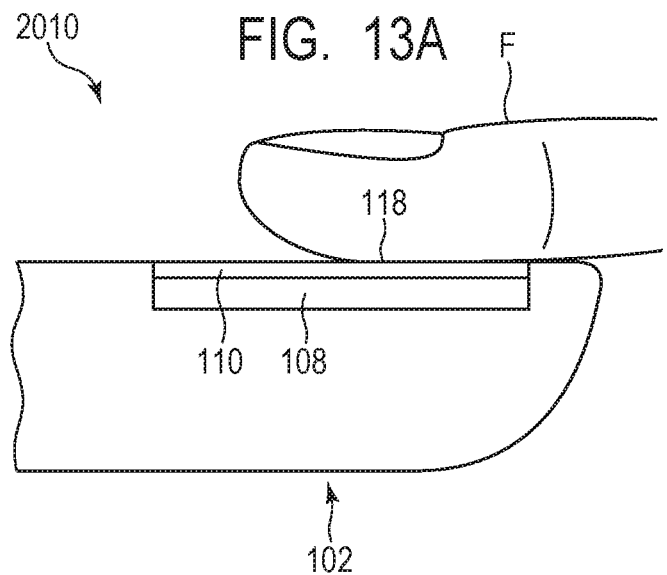
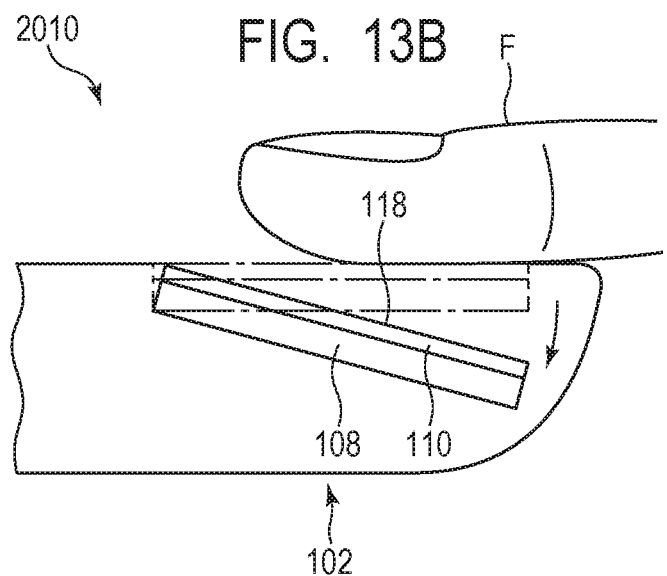
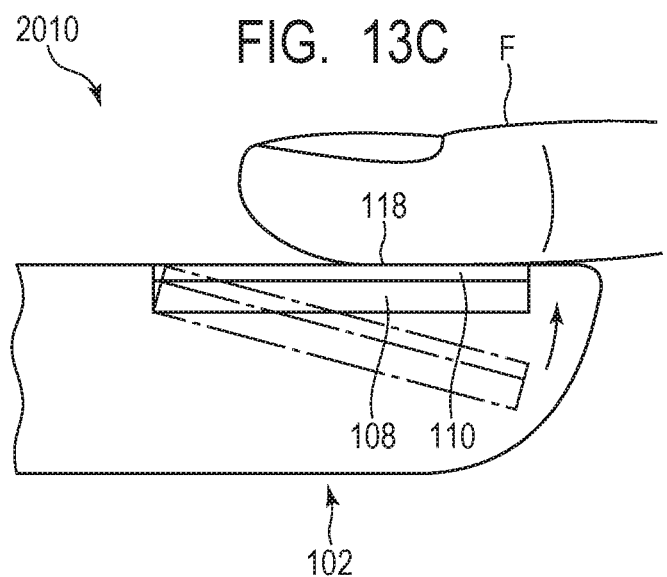

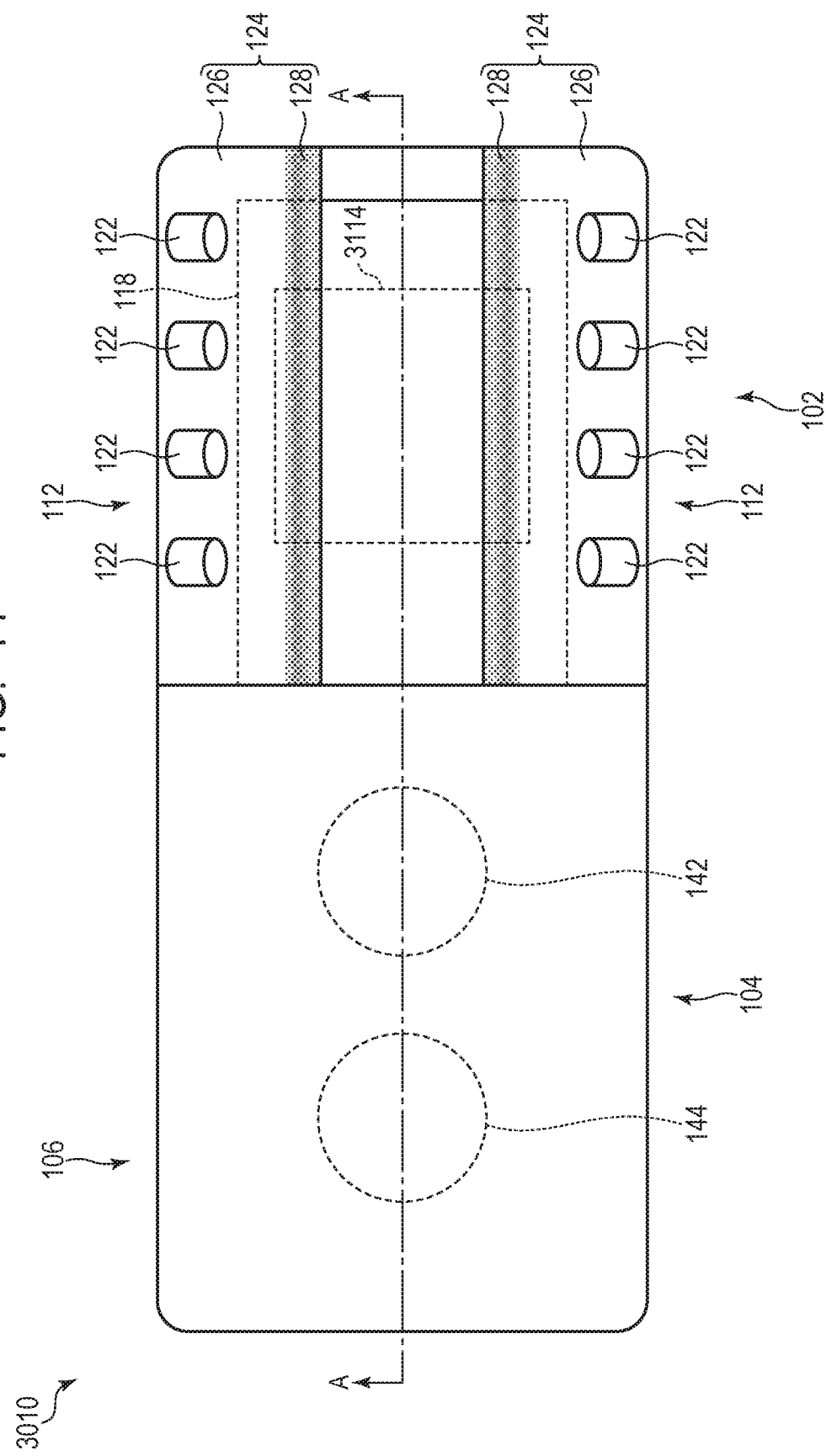

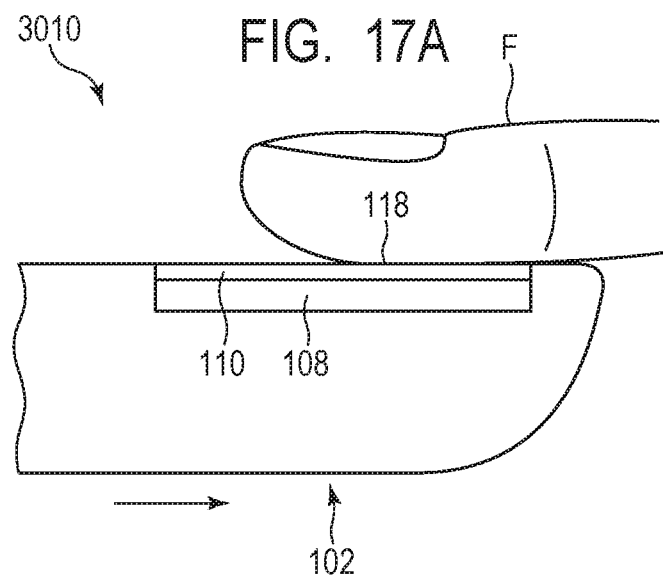
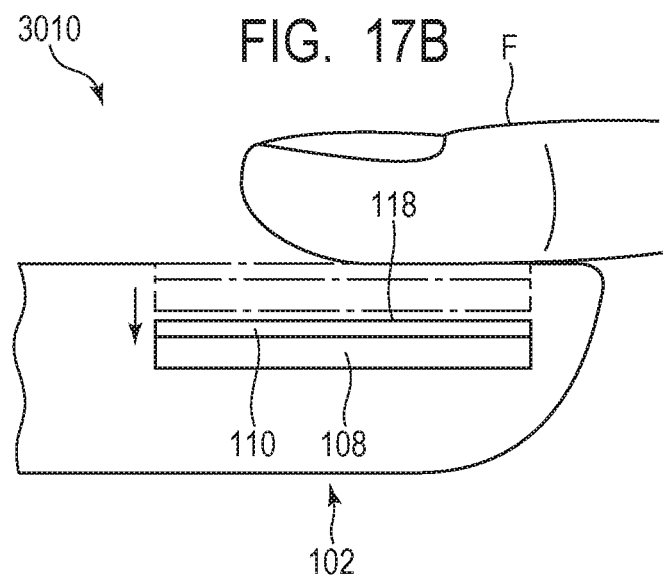
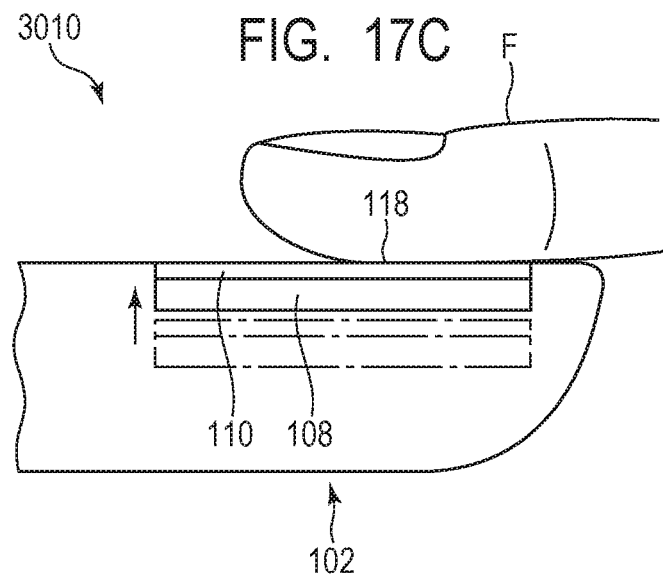

1

FINGERPRINT READING DEVICE AND FINGERPRINT READING METHOD

CROSS-REFERENCE TO RELATED APPLICATION

This application is a Continuation Application of U.S. application Ser. No. 16/313,743, filed on Dec. 27, 2018, which is a National Stage Entry of PCT/JP2018/027400, filed on Jul. 20, 2018, which claims the priority benefit of Japanese Patent Application No. 2017-144532, filed on Jul. 26, 2017, in the Japan Patent Office, the disclosure of which is incorporated herein by reference.

TECHNICAL FIELD

The present invention relates to a fingerprint reading device and a fingerprint reading method.

BACKGROUND ART

Fingerprints have uniqueness and permanence because fingerprints are different among individuals and do not change in their lifetime. Thus, fingerprints have been widely used in the situations where recognition of an individual is required.

As a device that reads a fingerprint as described above, a device of an optical type, an electrostatic capacitance type, and the like is known (see, Patent Literatures 1 to 4). For example, in a device of an optical type, a fingerprint is captured and read by using a two-dimensional image sensor such as a Complementary Metal Oxide Semiconductor (CMOS) image sensor or the like.

Among the optical devices that capture a fingerprint by using an image sensor, a transmission-type fingerprint input device has been focused on (see Patent Literatures 1 to 3). In a transmission-type fingerprint input device, a light from a light source is caused to enter a finger and is scattered therein, and a light exiting from the surface of the finger is utilized to capture an image of a fingerprint.

CITATION LIST

Patent Literature

PTL 1: International Publication WO2017/047090
PTL 2: International Publication WO2017/047091
PTL 3: International Publication WO2017/047092
PTL 4: Japanese Patent Application Laid-Open No. 2005-182474

SUMMARY OF INVENTION

Technical Problem

As described above, when a fingerprint is read by each of various schemes, in general, a finger from which a fingerprint is read is placed on a reading face on a reading sensor supported by the scheme, such as an image sensor, and the fingerprint is then read. In this case, for example, a relatively soft finger such as a wet finger, a finger with a high water-retention capability, a finger of a newborn or an infant may be significantly elastically deformed when a finger is placed on the reading face in a particular manner. Since it is difficult to appropriately read a fingerprint from a finger where large elastic deformation occurs, it is difficult to acquire a high quality fingerprint image that can be utilized for recognition of an individual or the like.

For example, when a reading face of a fingerprint reading image is slid onto a finger of a gripped hand to cause the finger to come into contact with a sensor face, if the finger in contact with the sensor face is relatively soft, the finger may be easily subjected to significant elastic deformation due to force received in a sliding direction of the reading face and other force.

An example object of the present invention is to provide a fingerprint reading device and a fingerprint reading method that can appropriately read a fingerprint even when reading a fingerprint of a relatively soft finger that may be easily subjected to significant elastic deformation.

Solution to Problem

According to one aspect of the present invention, provided is a fingerprint reading device including: a placement portion on which a finger is placed; a reading face provided on the placement portion so as to be able to move between a first position where the finger placed on the placement portion comes into contact with the reading face and a second position where the finger placed on the placement portion separates from the reading face; a drive unit that causes the reading face to move between the first position and the second position: and a reading unit that reads a fingerprint of the finger in contact with the reading face positioned at the first position, the drive unit causes the reading face in contact with the finger at the first position to move to the second position and further move from the second position to the first position, and the reading unit reads a fingerprint of the finger in contact with the reading face that has moved from the second position to the first position.

According to another aspect of the present invention, provided is a fingerprint reading method of reading a fingerprint of a finger in contact with a reading face provided on a placement portion so as to be able to move between a first position where the finger placed on the placement portion comes into contact with the reading face and a second position where the finger placed on the placement portion separates from the reading face, and the fingerprint reading method includes: placing the finger on the placement portion in which the reading face is positioned at the first position; causing the reading face in contact with the finger at the first position to move to the second position and further move from the second position to the first position; and reading a fingerprint of the finger in contact with the reading face that has moved from the second position to the first position.

Advantageous Effects of Invention

According to the present invention, it is possible to read the fingerprint appropriately even when reading a fingerprint of a relatively soft finger that may be easily subjected to significant elastic deformation.

BRIEF DESCRIPTION OF DRAWINGS

FIG. 6 is a schematic diagram illustrating a view in which a fingerprint of a finger of a subject is read by using the fingerprint reading device according to the first example embodiment of the present invention.

FIG. 8 is a block diagram illustrating an image processing apparatus according to the first example embodiment of the present invention.

FIG. 9A is a schematic diagram illustrating the operation of the fingerprint reading device according to the first example embodiment of the present invention.

FIG. 9B is a schematic diagram illustrating the operation of the fingerprint reading device according to the first example embodiment of the present invention.

FIG. 9C is a schematic diagram illustrating the operation of the fingerprint reading device according to the first example embodiment of the present invention.

FIG. 13A is a schematic diagram illustrating the operation of the fingerprint reading device according to the second example embodiment of the present invention.

FIG. 13B is a schematic diagram illustrating the operation of the fingerprint reading device according to the second example embodiment of the present invention.

FIG. 13C is a schematic diagram illustrating the operation of the fingerprint reading device according to the second example embodiment of the present invention.

FIG. 14 is a plan view illustrating a fingerprint reading device according to a third example embodiment of the present invention.

FIG. 17A is a schematic diagram illustrating the operation of the fingerprint reading device according to the third example embodiment of the present invention.

FIG. 17B is a schematic diagram illustrating the operation of the fingerprint reading device according to the third example embodiment of the present invention.

FIG. 17C is a schematic diagram illustrating the operation of the fingerprint reading device according to the third example embodiment of the present invention.

DESCRIPTION OF EMBODIMENTS

First Example Embodiment

A fingerprint reading device and a fingerprint reading method according to a first example embodiment of the present invention will be described by using FIG. 1 to FIG. 10C.

Figure 1:
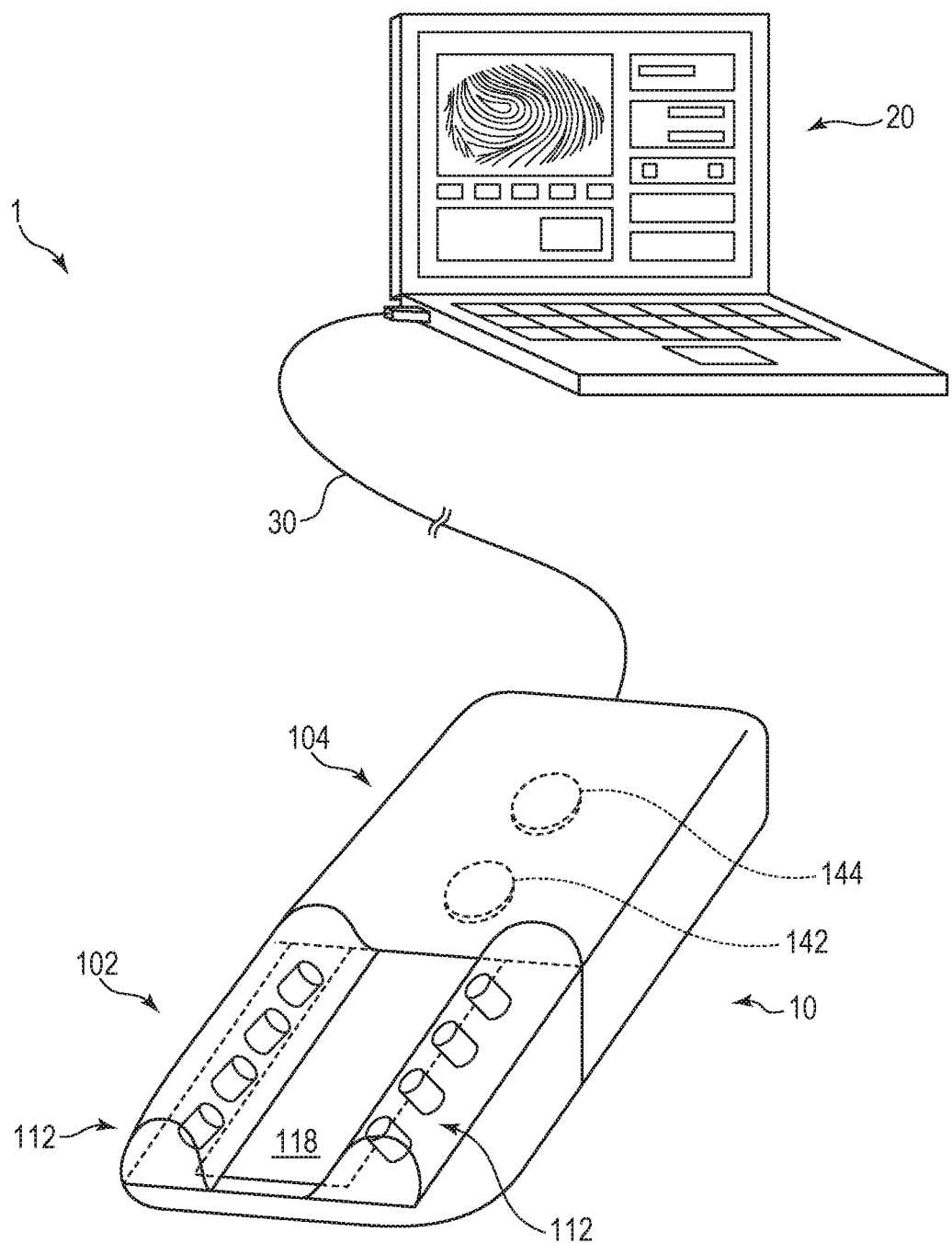
FIG. 1 is a schematic diagram illustrating a fingerprint reading system according to a first example embodiment of the present invention.

First, the general configuration of the fingerprint reading system including the fingerprint reading device according to the present example embodiment will be described by using FIG. 1. FIG. 1 is a schematic diagram illustrating the general configuration of the fingerprint reading system according to the present example embodiment.

As illustrated in FIG. 1, a fingerprint reading system 1 according to the present example embodiment has a fingerprint reading device 10 that captures and reads a fingerprint of a subject and an image processing apparatus 20 that performs processes such as display, recording, or the like on a fingerprint image that is an image of a fingerprint read by the fingerprint reading device 10. The fingerprint reading device 10 has a placement portion 102 on which a finger of a subject is placed and a holding portion 104 that is held by a user when used. A sensor face 118 with which a finger placed on the placement portion 102 comes into contact is provided on the placement portion 102. The fingerprint reading device 10 is communicatively connected to the image processing apparatus 20 via the communication cable 30. Note that the fingerprint reading device 10 may be communicatively connected to the image processing apparatus 20 by using a wireless scheme instead of a wired scheme through the communication cable 30.

The fingerprint reading device 10 according to the present example embodiment is targeted for a newborn, an infant, and a young child as a subject whose fingerprint is read, for example. A finger of a newborn, an infant, and a young child, in particular, a finger of a newborn has a higher moisture percentage and thus is softer than a finger of an adult, and a finger of a newborn may be more easily subjected to significant elastic deformation than a finger of an adult. The fingerprint reading device 10 according to the present example embodiment can appropriately read a fingerprint even in a case of a finger, such as a finger of a newborn, an infant, and a young child, which is relatively soft due to a high moisture percentage and may be easily subjected to significant elastic deformation, as described later. Note that it is impossible or difficult for a newborn, an infant, a young child, or the like to capture the fingerprint by himself/herself alone. When a fingerprint of such a subject who is unable to capture or has difficulty in capturing an image of the fingerprint by himself/herself alone is to be read, an adult or the like who is able to operate a device will be a user, and the user will have a fingerprint of a subject read, as described later.

The fingerprint reading device 10 is an optical fingerprint scanner that captures a fingerprint image by using a two-dimensional image sensor and reads a fingerprint. The fingerprint reading device 10 can capture a fingerprint image of any one of respective thumbs, index fingers, middle fingers, ring fingers, and little fingers of the left hand and the right hand of a subject, namely, the ten fingers in total, for example. Further, the fingerprint reading device 10 can capture a fingerprint image of not only a finger of the hands but also any one of respective first toes, second toes, third toes, fourth toes, and fifth toes of the left foot and the right foot, namely, the ten fingers of feet (toes) in total.

When a newborn, an infant, or a young child is a subject, for example, the fingerprint reading device 10 can be used to capture fingerprints of a plurality of fingers or toes of a single subject and provide these fingerprint images of the plurality of fingers or toes for recognition of an individual. In this case, for example, for a single subject, fingerprints of the thumb of the left hand, the thumb of the right hand, the first toe of the left foot, and the first toe of the right foot can be sequentially captured.

Figure 2:
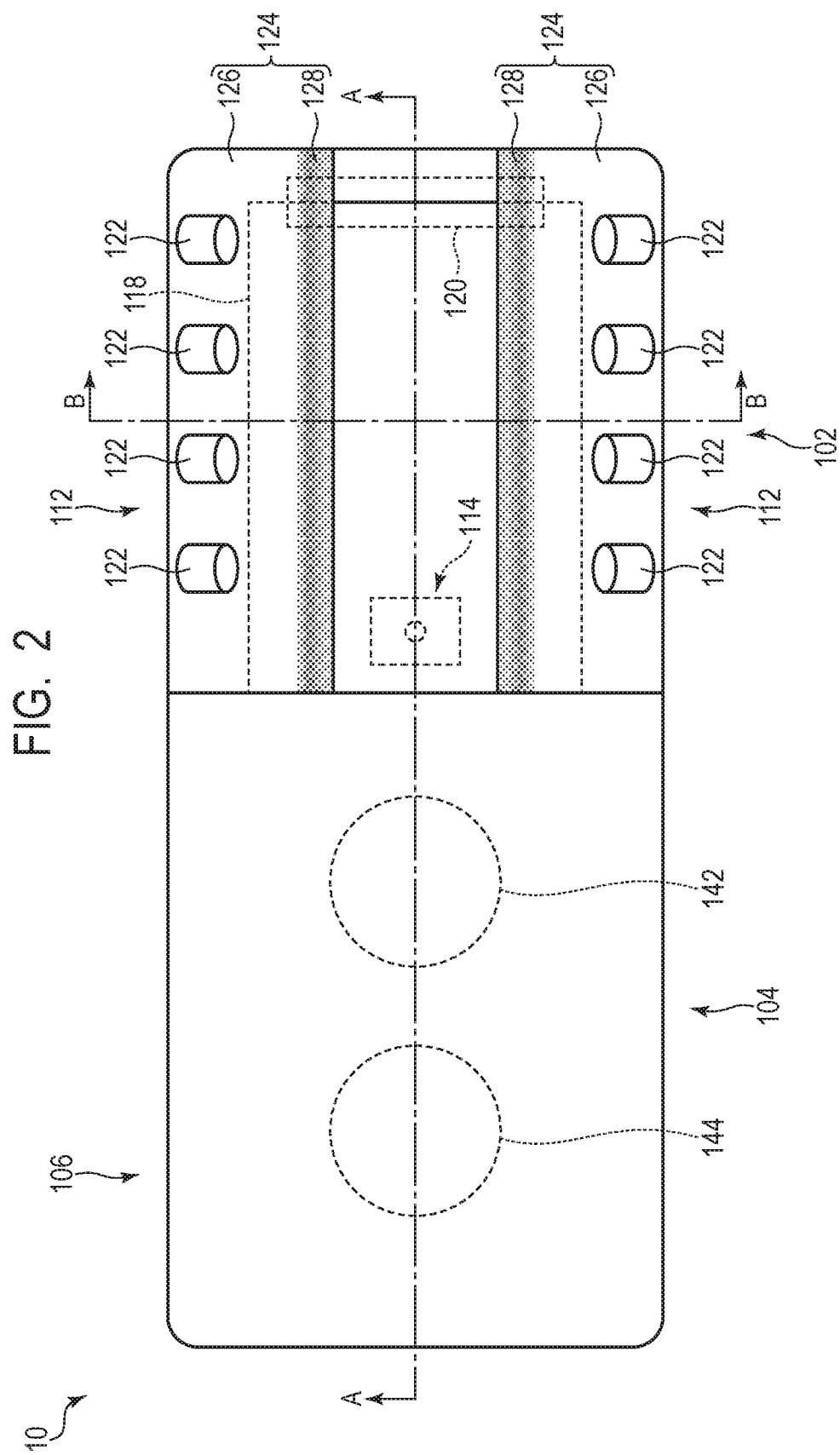
FIG. 2 is a plan view illustrating a fingerprint reading device according to the first example embodiment of the present invention.
Figure 3:
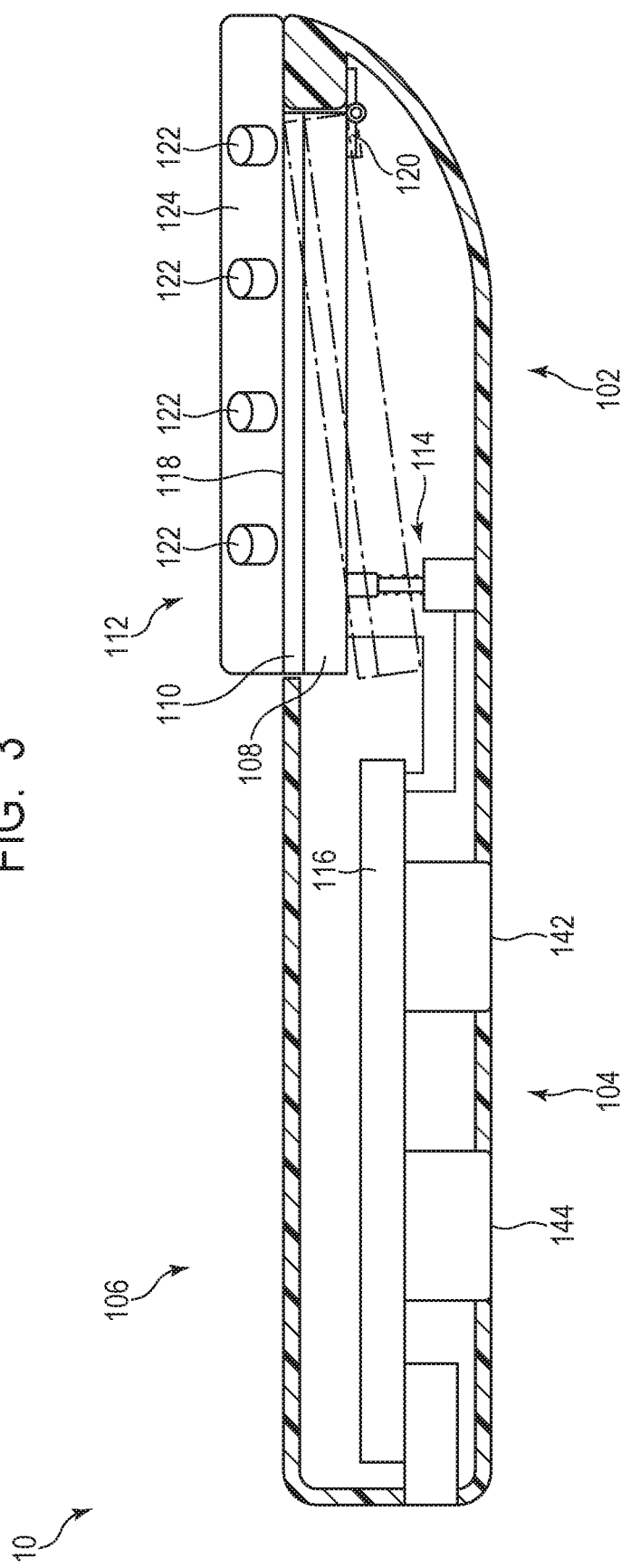
FIG. 3 is a longitudinal sectional view illustrating the fingerprint reading device according to the first example embodiment of the present invention.
Figure 4:
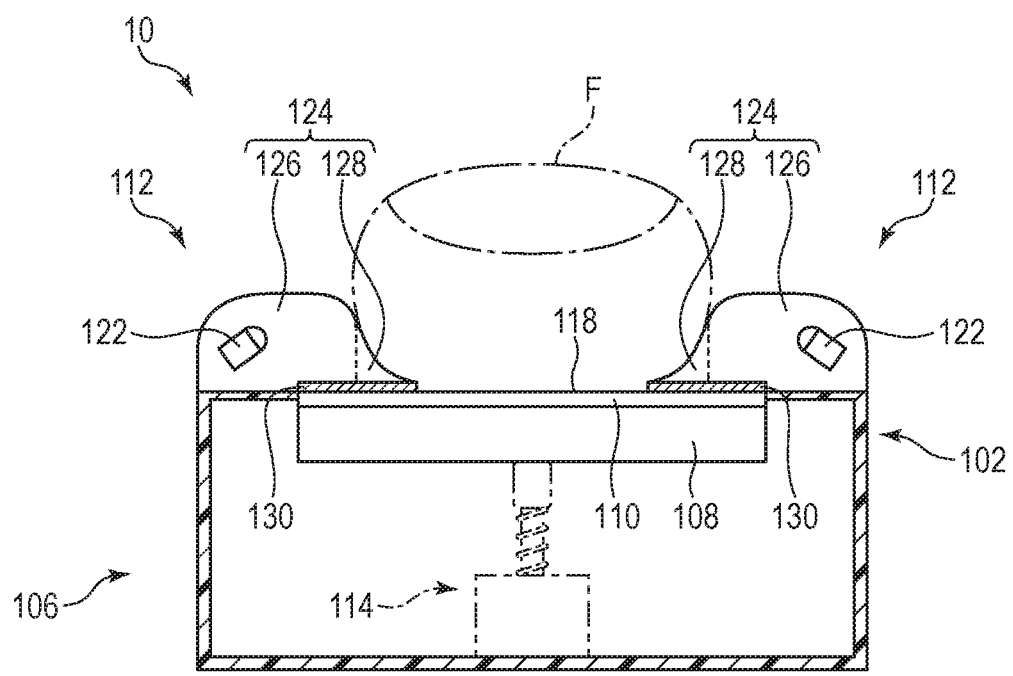
FIG. 4 is a transverse sectional view illustrating the fingerprint reading device according to the first example embodiment of the present invention.
Figure 5A:
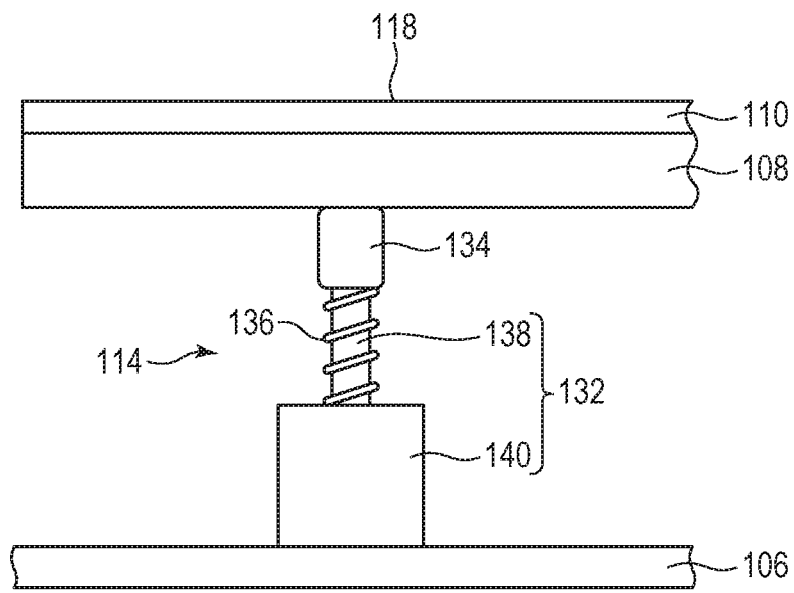
FIG. 5A is a schematic diagram illustrating an example of a sensor drive unit in the fingerprint reading device according to the first example embodiment of the present invention.
Figure 5B:
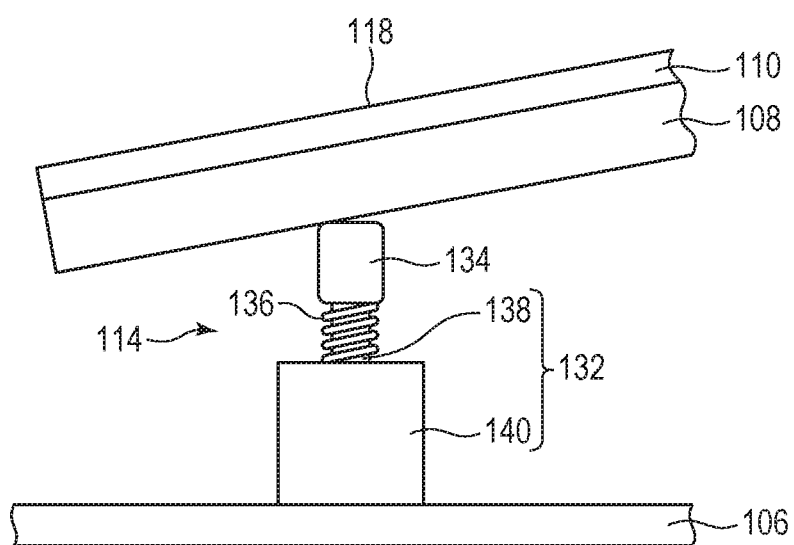
FIG. 5B is a schematic diagram illustrating an example of the sensor drive unit in the fingerprint reading device according to the first example embodiment of the present invention.
Figure 7:
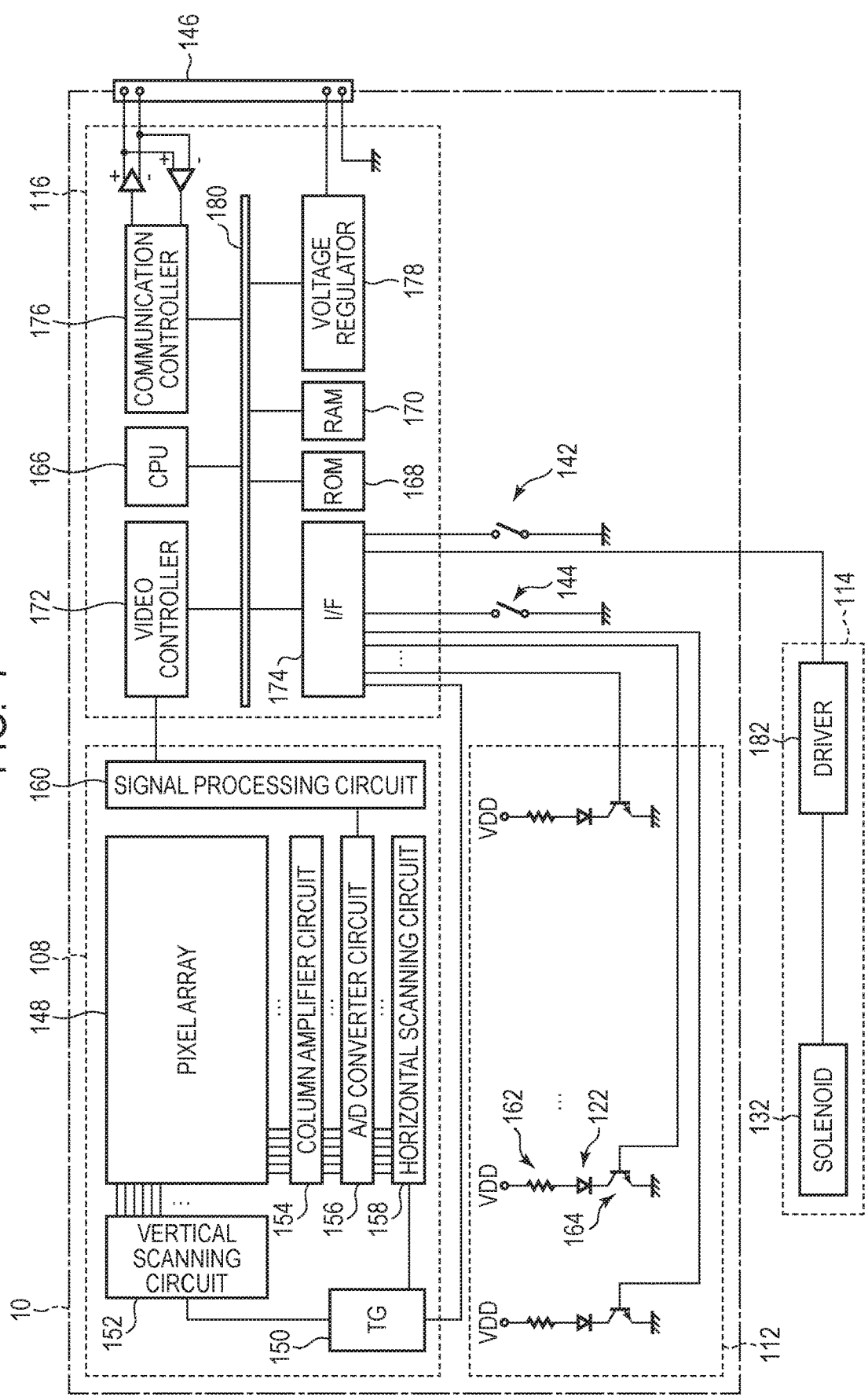
FIG. 7 is a block diagram illustrating the fingerprint reading device according to the first example embodiment of the present invention.

A specific configuration of the fingerprint reading device 10 according to the present example embodiment will be further described below by using FIG. 2 to FIG. 7. FIG. 2 is a plan view illustrating the fingerprint reading device 10 according to the present example embodiment, which illustrates a plane viewed from a top face side out of the front face and the back face of the fingerprint reading device 10. FIG. 3 is a longitudinal sectional view illustrating the fingerprint reading device 10 according to the present example embodiment, which illustrates a vertical cross section taken along a line A-A of FIG. 2. FIG. 4 is a horizontal cross section illustrating the fingerprint reading device 10 according to the present example embodiment, which illustrates a horizontal cross section taken along a line B-B of FIG. 2. FIG. 5A and FIG. 5B are schematic diagrams illustrating an example of a sensor drive unit in the fingerprint reading device 10 according to the present example embodiment. FIG. 6 is a schematic diagram illustrating a view in which a fingerprint of a finger of a subject is read by using the fingerprint reading device 10 according to the present example embodiment. FIG. 7 is a block diagram illustrating the fingerprint reading device 10 according to the present example embodiment. Note that, in the first example embodiment and subsequent example embodiments, the scale of each member is not the same in each referenced drawing, and each member may be depicted with exaggeration for the purpose of illustration.

As illustrated in FIG. 2 to FIG. 4, the fingerprint reading device 10 according to the present example embodiment has a casing 106, an image sensor 108, a sensor cover 110, a pair of side light sources 112, a sensor drive unit 114, and a control circuit 116.

A casing 106 is a hollow member having an external shape of a vertically flat, thin, approximate rectangular parallelepiped, and the longitudinal direction thereof is a front-rear direction. The casing 106 is made of a resin, for example. Of the front-side part and the rear-side part along the longitudinal direction of the casing 106, the front-side part is the placement portion 102, and the rear-side part is the holding portion 104. The front end part of the placement portion 102 has a tapered shape inclined from the backside face side to the top face side. Note that the external shape of the casing 106 is not limited to the external shape of a flat, approximate rectangular parallelepiped, but any shape may be employed.

The image sensor 108 is provided inside the casing 106 of the placement portion 102. The image sensor 108 is arranged such that the image capturing surface thereof faces the outside of the casing 106. A sensor cover 110 is provided on the image capturing surface of the image sensor 108.

The surface of the sensor cover 110 forms the sensor face 118 that is a reading face on which a ball of a finger of a subject whose fingerprint is to be read is placed and with which the placed ball of the finger comes into contact. The sensor cover 110 is formed of a plate-like member made of a material that transmits a near-infrared light, for example, formed of a protection glass. Thereby, as described later, a near-infrared light is emitted from the pair of side light sources 112 and enters the finger on the sensor cover 110, and the near-infrared light emitted from the ball side of the finger enters the image sensor 108 after scattering inside the finger.

The image capturing face of the image sensor 108 has a rectangular planar shape having a larger area than the ball of a finger (toe) whose fingerprint is to be captured. At a capturing position described later, the image sensor 108 is arranged such that the longitudinal direction of the rectangular planar shape is in parallel to the front-rear direction of the casing 106. Note that the planar shape of the image sensor 108 is not particularly limited, but various shapes may be employed. Further, a heatsink made of a metal or the like used for cooling the image sensor 108 may be provided on the backside face of the image sensor 108.

The image sensor 108 functions as a reading unit that reads a fingerprint of a finger. The image sensor 108 is configured to capture and read a fingerprint of a finger by receiving, on the image capturing face, a near-infrared light that has been emitted from the ball of the finger in contact with the sensor face 118 of the sensor cover 110 and has transmitted through the sensor cover 110, as described later. The image sensor 108 is a two-dimensional image sensor, for example, a CMOS image sensor. Further, as the image sensor 108, a Charge Coupled Device (CCD) image sensor may be used other than the CMOS image sensor. While the pixel density and the number of pixels of the image sensor 108 are not particularly limited, for example, a high density such as 1000 ppi or higher and a large number of pixels are preferable in taking into consideration of a case of capturing a fingerprint of a newborn, an infant, a young child, or the like. Specifically, for example, a CMOS image sensor having a large size of a width of 20 mm and a length of 30 mm, a high pixel density of 1270 ppi, and a large number of pixels can be used as the image sensor 108.

The front end part of the image sensor 108 is attached to a top plate at the front end of the placement portion 102 in the casing 106 via a hinge part 120. The hinge part 120 includes a rocking shaft extending in the width direction of the placement portion 102 in the casing 106. Note that the front side or the front end part of the image sensor 108 refers to the end part of the fingerprint reading device 10, that is, the end part, which is located opposite to the holding portion 104, of the placement portion 102. Further, the rear side or the rear end part of the image sensor 108 refers to the center part of the fingerprint reading device 10, that is, the end part, which is located on the holding portion 104 side, of the placement portion 102.

The image sensor 108 and the sensor cover 110 including the sensor face 118 are provided so as to be able to swing about a rocking shaft of the hinge part 120 located at the front side end of the placement portion 102 as a fulcrum. This enables the image sensor 108 and the sensor cover 110 including the sensor face 118 to move between a capturing position, which is a first position, and a recessed position, which is a second position located inside the casing 106 deeper than the capturing position.

At the capturing position, the image sensor 108 and the sensor cover 110 are arranged such that the sensor face 118 of the sensor cover 110 is orthogonal to the perpendicular direction of the placement portion 102. Further, the image sensor 108 and the sensor cover 110 positioned at the capturing position seal the inside of the placement portion 102. On the other hand, at the recessed position, the image sensor 108 and the sensor cover 110 are arranged such that the sensor face 118 of the sensor cover 110 is inclined to face the rearward oblique upper direction relative to the placement portion 102.

The image sensor 108 and the sensor cover 110 including the sensor face 118 are driven by the sensor drive unit 114 and move between the capturing position and the recessed position. At the capturing position, the sensor face 118 contacts with the ball of the finger placed on the placement portion 102. In contrast, at the recessed position, the sensor face 118 separates from the ball of the finger placed on the placement portion 102.

In FIG. 3, the image sensor 108 and the sensor cover 110 at the capturing position are illustrated by the solid line, and the image sensor 108 and the sensor cover 110 at the recessed position are illustrated by the one-dot-chain line. As illustrated, the sensor face 118 of the sensor cover 110 at the capturing position is orthogonal to the perpendicular direction of the placement portion 102 and forms a flat face with the surface of the holding portion 104 with substantially no step. On the other hand, the sensor face 118 of the sensor cover 110 at the recessed position is inclined so as to enter the inside of the casing 106 in the direction from the front side to the rear side of the placement portion 102.

The pair of side light sources 112 are provided above regions on both sides of the sensor face 118 in the placement portion 102 of the casing 106. Each of the pair of the side light sources 112 forms a line light source provided so as to extend in the front-rear direction of the placement portion 102 that is the longitudinal direction of the casing 106. The pair of side light sources 112 are provided on both end portions of the sensor face 118, which are opposed to each other in the width direction of the placement portion 102, and face each other in the width direction of the placement portion 102 via the sensor face 118. Each of the pair of side light sources 112 is a light source that irradiates a finger placed on the sensor face 118 of the placement portion 102 with near-infrared light.

Each side light source 112 has a plurality of near-infrared LEDs 122 and light guiding parts 124 formed to cover the plurality of near-infrared LEDs 122. In each side light source 112, the plurality of near-infrared LEDs 122 are arranged so as to be aligned in a line in the front-rear direction of the placement portion 102. The plurality of near-infrared LEDs 122 arranged in each line are covered with the light guiding part 124 provided in the front-rear direction of the placement portion 102.

Each of the plurality of near-infrared LEDs 122 forms a unit light source forming a line light source, respectively, and emits near-infrared light of a wavelength of 820 to 980 nm for example. Each near-infrared LED 122 is provided at the same height as the sensor face 118 in the capturing position or a height higher than the sensor face 118 at the capturing position in the perpendicular direction of the casing 106. Further, each near-infrared LED 122 is arranged inclined such that the light axis thereof is oriented to the center upper space of the sensor face 118 at the capturing position. Each near-infrared LED 122 is arranged inclined such that the angle of the light axis relative to the sensor face 118 is greater than 0 degree and less than 90 degrees, for example.

With each near-infrared LED 122 being arranged inclined in such a way, each of the side light sources 112, which is a line light source, is configured such that the light axis thereof is inclined inward above the sensor face 118 positioned at the capturing position and oriented to the center upper space of the sensor face 118. Each side light source 112 is arranged such that the angle of the light axis relative to the sensor face 118 is greater than 0 degree and less than 90 degrees, for example. With the light axis of each side light source 112 being inclined inward above the sensor face 118 as discussed above, each of the side light sources 112 is able to irradiate a finger placed on the sensor face 118 of the placement portion 102 with a sufficient light amount of near-infrared light.

The light guiding part 124 is formed of a light-transmitting resin such as a silicone, for example, or other light-transmitting materials. Note that the light-transmitting material forming the light guiding part 124 is not particularly limited as long as it has a transmittance to the near-infrared light emitted from the plurality of near-infrared LEDs 122, and various light-transmitting materials may be used.

The light guiding parts 124 are formed in the front-rear direction of the placement portion 102 so as to cover the plurality of near-infrared LEDs 122 that form a plurality of unit light sources each aligned in a line in the front-rear direction of the placement portion 102. The light guiding part 124 covering the plurality of near-infrared LEDs 122 scatters and guides near-infrared lights emitted from the plurality of near-infrared LEDs 122 and emits the near-infrared lights to a finger placed on the sensor face 118 of the placement portion 102.

Each of the light guiding parts 124 has a ridge-like protrusion part 126 and a skirt-like edge part 128 formed integrally with the protrusion part 126. The protrusion part 126 is formed in a ridge-like manner so as to cover the plurality of near-infrared LEDs 122 and protrude above the placement portion 102. The edge part 128 is formed in a skirt-like manner integrally with the protrusion part 126 so as to extend on the sensor face 118 side of the protrusion part 126 continuously from the protrusion part 126 on the sensor face 118 side. The edge part 128 has a lower height in the perpendicular direction of the placement portion 102 than the protrusion part 126, and the height thereof gradually decreases toward the sensor face 118 side.

The protrusion part 126 has a convex surface protruding to the upward side of the placement portion 102 that is the opposite side of the sensor face 118, for example. On the other hand, the edge part 128 has a convex surface protruding to the downward side of the placement portion 102 that is the sensor face 118 side, for example.

Each of the light guiding parts 124 is formed so as to partially protrude and extend up to above the end of the sensor face 118. More specifically, in the light guiding part 124, the edge part 128 and a part of the protrusion part 126 on the edge part 128 side protrude over the end of the sensor face 118 and are located on the end of the sensor face 118. The partially protruding light guiding part 124 as discussed above is configured such that the surface thereof on the sensor face 118 side comes into contact with the surface of a finger on the sensor face 118 side placed on the sensor face 118. As discussed above, by being formed so as to partially protrude and extend up to above the end of the sensor face 118, the light guiding part 124 is configured to be able to support a finger placed on the placement portion 102.

The protrusion width, which is a width formed of the edge part 128 and a part of the protrusion part 126 on the edge part 128 side protruding and located over the end of the sensor face 118, is constant over the front-rear direction of the placement portion 102. The protrusion width of the edge part 128 and a part of the protrusion part 126 on the edge part 128 side is not particularly limited and can be appropriately set in accordance with the size of a finger of the age group of a subject or the like. For example, when a newborn is a subject, each of the light guiding parts 124 on both sides may be configured such that the protrusion width of the edge part 128 and a part of the protrusion part 126 on the edge part 128 side is 5 mm, respectively, with respect to the image sensor 108 of a width of 20 mm. In this case, the width of the sensor face 118 exposed between both the edge parts 128 is 10 mm.

Light shielding parts 130 are each provided on the under surface, which is on the sensor face 118 side, of the edge part 128 and a part of the protrusion part 126, which is a part located protruding over the end of the sensor face 118 of the light guiding part 124. The under surface of the sensor face 118 side of the edge part 128 and a part of the protrusion part 126 provided with the light shielding part 130 is a flat surface parallel to the sensor face 118 at the capturing position.

The light shielding part 130 is provided for preventing the near-infrared light emitted from the near-infrared LEDs 122 from directly entering the image sensor 108 from the protrusion part 126 and the edge part 128 without passing through a finger. By using the light shielding part 130 to prevent the near-infrared light from directly entering the image sensor 108 without passing through a finger, it is possible to reduce a noise light and acquire a higher quality fingerprint image. Note that the light shielding part 130 may be of a reflection type that blocks near-infrared light by reflecting near-infrared light entering the light shielding part 130 or may be of an absorption type that blocks near-infrared light by absorbing near-infrared light entering the light shielding part 130. As the light shielding part 130, a film, a foil, a sheet, or other light shielding member made of a light shielding material that blocks near-infrared light by reflecting or absorbing the near-infrared light as discussed above can be used.

In the fingerprint reading device 10 according to the present example embodiment, in the light guiding part 124, a finger on the sensor face 118 can be irradiated with near-infrared lights not only from the protrusion part 126 but also from the edge part 128 that is closer to the sensor face 118 than the protrusion part 126. Furthermore, the edge part 128 or the edge part 128 and the protrusion part 126 is in contact with the surface, which is on the sensor face 118 side, of a finger placed on the sensor face 118. The use of the edge part 128 described above can increase the light amount of near-infrared light entering the finger on the sensor face 118. Therefore, according to the present example embodiment, a high quality fingerprint image with a high contrast can be acquired.

Further, the light guiding part 124 in each side light source 112 not only guides the near-infrared lights emitted from the plurality of near-infrared LEDs 122 as described above but also functions as a support part configured to be able to support a finger placed on the sensor face 118 of the placement portion 102. That is, in the light guiding part 124, the edge part 128 and a part of the protrusion part 126 located protruding over the end of the sensor face 118 contact with the surface of a finger F on the sensor face 118 side placed on the sensor face 118 and support the finger F from the sensor face 118 side, as illustrated in FIG. 4. With such light guiding part 124 being provided, it is possible to stably support a finger whose fingerprint is to be captured and suppress or even prevent displacement of the finger from the sensor face 118.

In particular, the fingerprint reading device 10 according to the present example embodiment is configured such that the image sensor 108 and the sensor cover 110 including the sensor face 118 move between the capturing position and the recessed position as described above. In such a configuration, the edge part 128 and a part of the protrusion part 126 contact with the surface of the finger F on the sensor face 118 side and support the finger F from the sensor face 118 side. This can suppress or even prevent displacement of the finger F due to motion of the image sensor 108 and the sensor cover 110. For example, even when the image sensor 108 and the sensor cover 110 move from the capturing position to the recessed position, displacement of the finger F due to the motion can be suppressed or even prevented.

The image sensor 108 captures and reads a fingerprint of a finger placed on the sensor face 118 at the capturing position. Here, the sensor drive unit 114 causes the sensor face 118 in contact with the finger at the capturing position to move from the capturing position to the recessed position and further move and return from the recessed position to the capturing position, as described later. In this case, the image sensor 108 captures and reads a fingerprint of the finger in contact with the sensor face 118 that has returned from the recessed position to the capturing position.

The image sensor 108 captures and reads a fingerprint by using a near-infrared light scattered inside a finger and emitted from the surface of the finger. The principle by which a fingerprint is captured by the image sensor 108 will be described below. When a fingerprint is captured, near-infrared lights are emitted from the pair of side light sources 112 with the ball of a finger being in contact with the sensor face 118 of the sensor cover 110. The near-infrared lights emitted from the pair of side light sources 112 that enter the finger on the sensor cover 110. The near-infrared lights that have entered the finger are scattered inside the finger and emitted outside the finger from the surface of the finger. The near-infrared lights emitted outside the finger have different intensities in accordance with whether emitted from the ridge part of the fingerprint or emitted from the valley part of the fingerprint.

Since the ridge part is in contact with the sensor face 118 of the sensor cover 110, the near-infrared light emitted outside the finger from the ridge part of the fingerprint reaches and enters the image sensor 108 with a relatively high intensity without significant attenuation. In contrast, since the valley part is not in contact with the sensor face 118, the near-infrared light emitted outside the finger from the valley part of the fingerprint is scattered by the air layer present between the valley part and the sensor face 118. In addition, reflection and refraction occurs due to a refractive index difference at the interface between the skin and the air and between the air and the sensor cover 110. Thus, the near-infrared light emitted from the valley part significantly attenuates compared to the near-infrared light emitted from the ridge part and reaches and enters the image sensor 108 with a relatively low intensity or is unable to reach the image sensor 108.

As a result, a fingerprint image in which a brightness difference is present between the ridge part and the valley part of the fingerprint is captured on the image sensor 108. That is, in the captured fingerprint image, the ridge part of the fingerprint corresponds to a bright part, and the valley part of the fingerprint corresponds to a dark part. The near-infrared lights scattered inside a finger and emitted outside the finger are received by the image sensor 108 in such a way, and thereby a fingerprint is captured.

The image sensor 108 that has captured a fingerprint of a finger outputs image data forming the fingerprint image. As described later, the image data output from the image sensor 108 is processed in the control circuit 116 and transferred to the image processing apparatus 20 via the communication cable 30. The image processing apparatus 20 to which the image data is transferred performs display, recording, or the like of the fingerprint image based on the transferred image data.

The sensor drive unit 114 is provided under the rear end part of the image sensor 108 inside the casing 106 of the placement portion 102. The sensor drive unit 114 is a drive unit that drives the rear end part of the image sensor 108, which is attached to the casing 106 so as to be able to swing, to move up and down and causes the image sensor 108 and the sensor cover 110 including the sensor face 118 to swing and move.

Specifically, the sensor drive unit 114 causes the rear end part of the image sensor 108 positioned at the capturing position to move down and causes the image sensor 108 and the sensor cover 110 including the sensor face 118 to swing and move from the capturing position to the recessed position. Further, the sensor drive unit 114 causes the rear end part of the image sensor 108 positioned at the recessed position to move up and causes the image sensor 108 and the sensor cover 110 including the sensor face 118 to swing and move from the recessed position to the capturing position. In such away, the sensor drive unit 114 causes the image sensor 108 and the sensor cover 110 including the sensor face 118 to move from the capturing position to the recessed position and further move and return from the recessed position to the capturing position.

The configuration of the sensor drive unit 114 is not limited to a particular configuration but may be any configuration that can move up and down the rear end part of the image sensor 108. For example, the sensor drive unit 114 may have a solenoid-type configuration in which a solenoid is used as an actuator. FIG. 5A and FIG. 5B illustrate an example having solenoid-type configuration as an example of the sensor drive unit 114. FIG. 5A is aside view illustrating a solenoid-type sensor drive unit 114 when the image sensor 108 is positioned at the capturing position. FIG. 5B is a side view illustrating a solenoid-type sensor drive unit 114 when the image sensor 108 is positioned at the recessed position.

As illustrated in FIG. 5A and FIG. 5B, the solenoid-type sensor drive unit 114 has a solenoid 132, a contact part 134, and an elastic member 136.

The solenoid 132 has a plunger 138 and a base part 140 including a coil, which is a pull-type solenoid in which the plunger 138 is pulled into the base part 140 in a conduction state. The base part 140 of the solenoid 132 is provided on the bottom of the casing 106 so that the plunger 138 operates in the perpendicular direction of the casing 106.

The contact part 134 is attached to the upper end of the plunger 138. The contact part 134 comes into contact with the underside of the rear end part of the image sensor 108 and supports the rear end part of the image sensor 108. The elastic member 136 such as a spring that actuates the contact part 134 to the image sensor 108 side is provided between the contact part 134 and the base part 140.

In a non-conduction state of the solenoid 132, as illustrated in FIG. 5A, the plunger 138 is not pulled into the base part 140. Furthermore, the contact part 134 is actuated to the image sensor 108 side by the elastic member 136. The contact part 134 actuated by the elastic member 136 comes into contact with the underside of the rear end part of the image sensor 108 and supports the rear end part of the image sensor 108. In the non-conduction state, the image sensor 108 and the sensor cover 110 including the sensor face 118 are positioned at the capturing position.

On the other hand, when a current is applied to the solenoid 132, the plunger 138 is pulled into the base part 140. When the plunger 138 is pulled into the base part 140, the contact part 134 moves down against the actuation force applied by the elastic member 136. In response, the rear end part of the image sensor 108 supported by the contact part 134 also moves down. Thus, the contact part 134 comes into contact with the underside of the rear end part of the image sensor 108 at a position lower than the position in the non-conduction state and supports the image sensor 108, as illustrated in FIG. 5B. In such a way, in the conduction state, the image sensor 108 and the sensor cover 110 including the sensor face 118 are positioned at the recessed position.

Furthermore, when the current applied to the solenoid 132 is stopped, pulling of the plunger 138 into the base part 140 is released. Furthermore, the plunger 138 and the contact part 134 move up due to the actuation force of the elastic member 136 to return to the initial position that is a non-conduction state. In response, the rear end part of the image sensor 108 supported by the contact part 134 also moves up. In such a way, in a non-conduction state after a conduction state, the image sensor 108 and the sensor cover 110 including the sensor face 118 return to the capturing position.

As discussed above, the solenoid-type sensor drive unit 114 moves down and up the rear end part of the image sensor 108 by using the contact part 134 attached to the plunger 138. Thereby, the sensor drive unit 114 causes the image sensor 108 and the sensor cover 110 including the sensor face 118 to swing and causes the image sensor 108 and the sensor cover 110 including the sensor face 118 to move between the capturing position and recessed position.

As described above, the solenoid-type one using the solenoid 132 can be used as the sensor drive unit 114. Note that the drive mechanism of the sensor drive unit 114 that moves the image sensor 108 and the sensor cover 110 is not limited to the electric mechanism using the solenoid 132 described above. The drive mechanism of the sensor drive unit 114 may be other electric mechanisms using a drive motor, a linear actuator, or the like that is driven electrically or may be a mechanical mechanism using a handle, a lever, a link, an arm, or the like that can be operated manually.

The holding portion 104 that is a rear side portion of the casing 106 is a portion held by the user who captures a finger of a subject whose fingerprint is to be captured when the fingerprint is captured.

A newborn, an infant, a young child, or the like is one who is unable to capture or has difficulty in capturing a fingerprint by himself/herself alone. Thus, a user who is an adult or a minor who is able to operate the device by himself/herself alone operates the fingerprint reading device 10 to capture a fingerprint of a finger of a subject who is a newborn, an infant, a young child, or the like. The user holds the holding portion 104 by one hand and moves the fingerprint reading device 10 from the front side thereof, namely, from the placement portion 102 toward the finger such as the thumb of the subject whose fingerprint is to be captured. The user is able to hold the holding portion 104 from the side such that, among the fingers of the hand holding the holding portion 104, the thumb is positioned on the top plate side of the casing 106 and the four fingers other than the thumb are positioned on the bottom plate side of the casing 106, for example. Furthermore, as illustrated in FIG. 6, the user is able to cause the ball of the finger of the subject to come into contact with the sensor face 118 of the sensor cover 110 while using the other hand if necessary. Note that, although not illustrated in FIG. 6, the user is able to use the fingertip of the thumb or the like of his/her hand which holds the holding portion 104 to press the finger of the subject that is in contact with the sensor face 118 and fix the position thereof.

A push button-type motion switch 142 is provided on the bottom face of the holding portion 104 held by the user. The motion switch 142 is configured to, when pressed, be able to drive the sensor drive unit 114 and move the image sensor 108 and the sensor cover 110 including the sensor face 118. That is, the motion switch 142 is configured to, when pressed, be able to cause the image sensor 108 and the sensor cover 110 to move from the capturing position to the recessed position and further move and return from the recessed position to the capturing position.

Further, a push button-type capture switch 144 is provided on the bottom face of the holding portion 104. The capture switch 144 is configured to, when pressed, be able to instruct the side light sources 112 to be turned on or off, instruct the image sensor 108 to capture a fingerprint, or instruct the image processing apparatus 20 to record a fingerprint image.

The user holding the holding portion 104 is able to press the motion switch 142 and the capture switch 144 by any of four fingers positioned on the bottom plate side of the casing 106 out of the fingers of a hand holding the holding portion 104 while holding the holding portion 104.

Further, the motion switch 142 is formed so as to be embedded in the holding portion 104 such that the pressing face of the motion switch 142 and the bottom face of the holding portion 104 are substantially flat with each other. Also, the capture switch 144 is formed so as to be embedded in the holding portion 104 such that the pressing face of the capture switch 144 and the bottom face of the holding portion 104 are substantially flat with each other. With the motion switch 142 and the capture switch 144 being provided so as not to protrude from the bottom face of the holding portion 104 in such a way, erroneous press of the motion switch 142 and the capture switch 144 can be suppressed.

The control circuit 116 is accommodated inside the holding portion 104 of the casing 106. Further, a connector unit 146 to which the communication cable 30 is connected is provided on the side end part on the rear side of the holding portion 104.

FIG. 7 is a block diagram illustrating respective components of the fingerprint reading device 10 described above, which illustrates the image sensor 108, the side light source 112, the sensor drive unit 114, and the control circuit 116 in detail.

As illustrated in FIG. 7, the image sensor 108 has a pixel array 148 and a timing generator 150. Further, the image sensor 108 has a vertical scanning circuit 152, a column amplifier circuit 154, an analog-to-digital (A/D) converter circuit 156, a horizontal scanning circuit 158, and a signal processing circuit 160.

A plurality of pixels are provided in a matrix in the pixel array 148. Each pixel has a photoelectric conversion element that generates a pixel signal by photoelectrically converting an incident near-infrared light. The timing generator 150 generates and outputs a timing signal used for controlling the vertical scanning circuit 152 and the horizontal scanning circuit 158. The vertical scanning circuit 152 scans the pixels of the pixel array 148 on a pixel row basis. The column amplifier circuit 154 amplifies pixel signals read by scans performed by the vertical scanning circuit 152. The A/D converter circuit 156 converts pixel signals amplified by the column amplifier circuit 154 from analog signals to digital signals. The horizontal scanning circuit 158 performs scans on a pixel column basis to read pixel signals converted by the A/D converter circuit 156 to the outside. The signal processing circuit 160 performs predetermined signal processing on the pixel signal read by the horizontal scanning circuit 158 and output from the A/D converter circuit 156 to output image data forming a fingerprint image. The image data output from the signal processing circuit 160 is input to the control circuit 116.

In the side light source 112, a current limiting resistor 162 that restricts a current flowing in the near-infrared LED 122 and a transistor 164 that serves as a switch are connected to each of the plurality of near-infrared LED 122.

One of the terminals of the current limiting resistor 162 is connected to the anode side terminal of each near-infrared LED 122. The collector of each transistor 164 is connected to the cathode side terminal of each near-infrared LED 122. A positive power source voltage VDD is input to the other terminal of each current limiting resistor 162. The base of each transistor 164 is connected to the control circuit 116, and the transistor 164 is switched to be turned on and off by a switch signal input to the base from the control circuit 116.

The control circuit 116 has a central processing unit (CPU) 166, a read only memory (ROM) 168, and a random access memory (RAM) 170. Further, the control circuit 116 has a video controller 172, an interface (I/F) 174, and a communication controller 176. Furthermore, the control circuit 116 has a voltage regulator 178. The CPU 166, the ROM 168, the RAM 170, the video controller 172, the I/F 174, and the communication controller 176 are connected to a common bus line 180.

The CPU 166 executes a program for controlling the operation of the fingerprint reading device 10 to control the operation of each unit of the fingerprint reading device 10. The ROM 168 stores a program executed by the CPU 166. Further, the RAM 170 is a working area when the CPU 166 executes a program.

The video controller 172 is connected to the signal processing circuit 160 of the image sensor 108, and image data is input from the signal processing circuit 160. The video controller 172 transfers image data to the communication controller 176 via the bus line 180.

The timing generator 150 of the image sensor 108 is connected to the I/F 174. Thereby, the control signal by the CPU 166 is input to the timing generator 150 via the I/F 174. The timing generator 150 generates and outputs a timing signal based on a control signal input via the I/F 174.

Further, the bases of the plurality of transistors 164 in the side light source 112 are connected to the I/F 174. Thereby, the switch signal from the CPU 166 is input to the base of the transistors 164 via the I/F 174. The transistor 164 is switched to be turned on and off based on a switch signal input via the I/F 174. In response to the transistor 164 being switched to be turned on and off, the near-infrared LED 122 is switched to be turned on and off, and thereby the side light source 112 is switched to be turned on and off.

The sensor drive unit 114 has the solenoid 132 and a driver 182 that controls driving of the solenoid 132. The driver 182 is connected to the I/F 174. Thereby, a control signal from the CPU 166 is input to the driver 182 via the I/F 174. The driver 182 controls driving of the solenoid 132 based on the control signal input via the I/F 174.

The motion switch 142 is connected to the I/F 174. The output of a control signal of the driver 182 from the CPU 166 is triggered in response to press of the motion switch 142.

Specifically, in a state before a fingerprint is read by the image sensor 108, the image sensor 108 and the sensor cover 110 including the sensor face 118 are positioned at the capturing position. When the motion switch 142 is pressed, the solenoid 132 is driven by the driver 182 in the sensor drive unit 114. Thereby, the image sensor 108 and the sensor cover 110 including the sensor face 118 move from the capturing position to the recessed position and further move and return from the recessed position to the capturing position.

Note that the motion switch 142 is not necessarily required to be provided. Instead, such a configuration is possible in which, in response to detection of contact of a finger with the sensor face 118, output of the control signal of the driver 182 is triggered, and the image sensor 108 and the sensor cover 110 including the sensor face 118 are moved from the capturing position toward the recessed position by the sensor drive unit 114, in the same manner as described above. In such a configuration without the motion switch 142 being provided, contact of the finger on the sensor face 118 can be detected based on a change in an image captured by the image sensor 108, for example, or can be detected by a sensor that can detect contact thereon, such as a touch sensor provided on the sensor face 118.

Further, the operating time period in which the image sensor 108 and the sensor cover 110 return to the capturing position via the recessed position from the capturing position is not particularly limited but may be set as appropriate. However, it is preferable to set this operating time period to a time period during which elastic deformation of a finger that once comes into contact with the sensor face 118 is sufficiently reduced.

Further, the capture switch 144 is connected to the I/F 174. In response to the capture switch 144 being pressed, output of a control signal of the image sensor 108 and a switch signal of the side light source 112 from the CPU 166 are triggered.

Specifically, in a non-operating state of the image sensor 108, the side light source 112 is also in a turn-off state, and when the capture switch 144 is pressed under this state, the side light source 112 is turned off and the image sensor 108 starts capturing a fingerprint. The image sensor 108 that has captured a fingerprint outputs image data of the captured fingerprint image. After outputting the image data, the image sensor 108 is in a non-operating state, and the side light source 112 is in a turn-off state. The image data of the fingerprint image output by the image sensor 108 is transferred to the image processing apparatus 20.

The communication controller 176 functions as a transfer unit that transfers image data of the fingerprint image, which transfers image data transferred from the video controller 172 to the image processing apparatus 20 via the communication cable 30 connected to the connector unit 146. The communication controller 176 is configured to communicate with the image processing apparatus 20 via the communication cable 30 in accordance with a communication standard such as Universal Serial Bus (USB) or the like, for example.

The communication cable 30 is configured to have two differential signal lines for transmitting and receiving signals, a power source line for power supply, and a ground line. The communication controller 176 transmits and receives signals through the two differential signal lines in the communication cable 30.

The power source line of the communication cable 30 is connected to the voltage regulator 178, and power is supplied via the power source line from a power source circuit 216 (see FIG. 8) in the image processing apparatus 20. The voltage regulator 178 adjusts the voltage of the supplied power and supplies it as a power source to each unit of the fingerprint reading device 10. The fingerprint reading device 10 is of a bus-power system so as to operate by power supplied via the communication cable 30 from the image processing apparatus 20 in such a way. Note that the fingerprint reading device 10 may be operated by power supplied from a built-in battery, for example, without limited to the bus-power system.

On the other hand, the image processing apparatus 20 functions as an image processing unit that performs processes such as display, recording, or the like on a fingerprint image transferred from the fingerprint reading device 10 that has captured a fingerprint. The image processing apparatus 20 may be formed of a personal computer (PC) device of a laptop type, a tablet type, or the like, for example. Further, image processing apparatus 20 can control the operation of the fingerprint reading device 10. Note that the image processing apparatus 20 is not necessarily required to include the display 214 described later, and the image processing unit can be configured as including no display unit.

The specific configuration of the image processing apparatus 20 will be further described below by using FIG. 8. FIG. 8 is a block diagram illustrating the image processing apparatus 20.

As illustrated in FIG. 8, the image processing apparatus 20 has a CPU 202, a ROM 204, a RAM 206, a hard disk drive (HDD) 208, and a communication controller 210. Further, the image processing apparatus 20 has a display controller 212 and the display 214. Further, the image processing apparatus 20 has the power source circuit 216 and an input device 218. The CPU 202, the ROM 204, the RAM 206, the HDD 208, the communication controller 210, display controller 212, the power source circuit 216, and the input device 218 are connected to a common bus line 220. Further, a connector unit 222 to which the communication cable 30 is connected is provided to the image processing apparatus 20.

The CPU 202 controls the entire operation of the image processing apparatus 20. Further, the CPU 202 executes an image processing program used for display, recording, or the like of a fingerprint image acquired by the fingerprint reading device 10. The image processing program performs image processing on image data transferred from the fingerprint reading device 10 and performs display, recording, or the like of a fingerprint image thereof.

The ROM 204 stores therein a program such as a boot program. The RAM 206 is used as a working area when the CPU 202 executes a process. Further, the RAM 206 functions as an image memory in which image data of a fingerprint image transferred from the fingerprint reading device 10 is temporarily stored. The HDD 208 stores a program such as an image processing program executed by the CPU 202.

Further, the HDD 208 functions as a recording unit that records a fingerprint image captured by the fingerprint reading device 10. The CPU 202 functions as a record control unit to record a fingerprint image in the HDD 208. Note that the recording unit that records a fingerprint image is not limited to the HDD 208 and, instead of the HDD 208, various recording devices may be used as the recording unit. The recording unit that records a fingerprint image may be built in the image processing apparatus 20 similarly to the HDD 208 or may be an independent external recording device separate from the image processing apparatus 20.

The communication controller 210 functions as a receiving unit that receives image data of a fingerprint image to receive image data transferred from the communication controller 176 of the fingerprint reading device 10 via the communication cable 30 connected to the connector unit 222. The image data received by the communication controller 210 is temporarily stored in the RAM 206 as an image memory. The communication controller 210 is configured to communicate with the fingerprint reading device 10 via the communication cable 30 in accordance with a communication standard such as USB or the like, for example, in association with the communication controller 176. The communication controller 210 is configured to transmit and receive signals by two differential signal lines in the communication cable 30 in association with the communication controller 176.

The display 214 that functions as a display unit that displays a fingerprint image is connected to the display controller 212. The display controller 212 cooperates with the CPU 202 to function as a display control unit and renders and displays a display window of an image processing program executed by the CPU 202 on the display 214. The display window of the image processing program displayed on the display 214 includes a preview window in which a captured fingerprint image is displayed. Note that, while not limited in particular, the display 214 is a liquid crystal display, for example. Further, the display 214 may be built in the image processing apparatus 20, which is a laptop PC, a tablet PC, or the like, or may be an external display provided separately from the image processing apparatus 20.

The power source circuit 216 supplies power of a built-in power source of the image processing apparatus 20 or power of an external power source connected to the image processing apparatus 20 to the fingerprint reading device 10.

The power source circuit 216 is connected to the power source line and the ground line of the communication cable 30 and supplies power to the voltage regulator 178 of the fingerprint reading device 10 via the power source line.

The input device 218 is a keyboard, a mouse, or the like, for example. Further, the input device 218 may be a touch panel embedded in the display 214. An operator can input text information such as an identification number (ID), a name, or the like of a subject or select information regarding the type of a finger in the image processing program displayed on the display 214 via the input device 218. Further, setting of capturing conditions or the like may be performed.

The fingerprint reading system 1 according to the present example embodiment is configured as described above.

Figure 10A:
FIG. 10A is a schematic diagram illustrating the principle by which deformation of a fingerprint is reduced when the fingerprint is read by using the fingerprint reading device according to the first example embodiment of the present invention.
Figure 10B:
FIG. 10B is a schematic diagram illustrating the principle by which deformation of a fingerprint is reduced when the fingerprint is read by using the fingerprint reading device according to the first example embodiment of the present invention.
Figure 10C:
FIG. 10C is a schematic diagram illustrating the principle by which deformation of a fingerprint is reduced when the fingerprint is read by using the fingerprint reading device according to the first example embodiment of the present invention.

Next, the operation of the fingerprint reading device 10 according to the present example embodiment will be further described by using FIG. 9A to FIG. 9C and FIG. 10A to FIG. 10C. FIG. 9A to FIG. 9C are schematic diagrams illustrating the operation of the fingerprint reading device 10 according to the present example embodiment. FIG. 9A to FIG. 9C illustrate the positional relationship of the finger F with the image sensor 108 and the sensor cover 110 after the finger F comes into contact with the sensor face 118 and before a fingerprint is captured. For simplified illustration, the side light sources 112 are omitted in FIG. 9A to FIG. 9C. FIG. 10A to FIG. 10C are schematic diagrams illustrating the principle by which elastic deformation of a fingerprint is reduced when the fingerprint is read by the fingerprint reading device 10 according to the present example embodiment. FIG. 10A is a schematic diagram schematically illustrating an ideal fingerprint to be read. FIG. 10B is a schematic diagram schematically illustrating a fingerprint to be read from a finger which is subjected to significant elastic deformation. FIG. 10C is a schematic diagram schematically illustrating a fingerprint to be read from a finger in which elastic deformation has been reduced.

In a state where the operation of the fingerprint reading device 10 is stopped, the image sensor 108 and the sensor cover 110 including the sensor face 118 are positioned at the capturing position. First, in a state where the image sensor 108 and the sensor cover 110 are positioned at the capturing position, the user causes the ball of the finger F of the subject to come into contact with the sensor face 118 of the fingerprint reading device 10, as illustrated in FIG. 9A. For example, the sensor face 118 is slid onto the ball of the finger F from the front side of the placement portion 102, which is the front side of the casing 106, so that the finger F is directed in the longitudinal direction of the casing 106, that is, the front-rear direction of the placement portion 102, and thereby the ball of the finger F comes into contact with the sensor face 118.

In a state where the ball of the finger F is in contact with the sensor face 118, for each of the pair of side light sources 112, the edge part 128 and a part of the protrusion part 126 located protruding over the end of the sensor face 118 come into contact with the surface of the finger F on the sensor face 118 side placed on the sensor face 118. The edge part 128 and a part of the protrusion part 126 in contact with the surface on the sensor face 118 side of the finger F support the finger F in contact with the sensor face 118 from the sensor face 118 side.

When the finger F comes into contact with the sensor face 118 as described above, however, a large elastic deformation may occur in the finger F in contact with the sensor face 118 due to force received in a sliding direction of the sensor face 118 and other force. In particular, in a case of the finger F such as a finger of a newborn or an infant, because of a high moisture percentage, the finger F is relatively soft, and large elastic deformation may occur. Further, when the sensor face 118 is slid onto the ball of the finger F as described above, a portion on the tip side of the finger F will receive force over longer time in a sliding direction of the sensor face 118 than a portion on the base side. Thus, more significant elastic deformation may occur in the portion on the tip side of the finger F than in the portion on the base side.

When a fingerprint is read in a state where large elastic deformation occurs in the finger F, the read fingerprint is significantly deformed entirely or locally and is fully different from the ideal fingerprint. For example, compared to the ideal fingerprint illustrated in FIG. 10A, a fingerprint read from the finger F where large elastic deformation occurs shrinks entirely in the sliding direction of the sensor face 118, that is, the longitudinal direction of the finger F as illustrated in FIG. 10B. Note that a fingerprint may not only shrink but also deform in various manners such as expanding, bending, or the like in response to force applied to the finger F. Further, a fingerprint may be deformed entirely as illustrated in FIG. 10B, or a part thereof may be deformed locally.

Next, in a state where the ball of the finger F is in contact with the sensor face 118, the user may press the motion switch 142. With the motion switch 142 being pressed, a drive instruction signal is input to instruct the fingerprint reading device 10 to drive the image sensor 108 and the sensor cover 110.

The CPU 166 of the fingerprint reading device 10 drives the sensor drive unit 114 in response to the drive instruction signal input by press of the motion switch 142 and drives the image sensor 108 and the sensor cover 110 including the sensor face 118. Thereby, the image sensor 108 and the sensor cover 110 including the sensor face 118 swing about a rocking shaft of the hinge part 120 attached to the casing 106 of the front end part of the image sensor 108 as a fulcrum.

Note that, in a configuration without the motion switch 142 being provided, in response to detection of contact of the ball of the finger F with the sensor face 118 instead of the motion switch 142 being pressed, the drive instruction signal is input, and the image sensor 108 and the sensor cover 110 including the sensor face 118 are driven by the sensor drive unit 114 in the same manner as described above.

The image sensor 108 and the sensor cover 110 including the sensor face 118 that swing first move from the capturing position to the recessed position with the rear end part thereof moving down, as illustrated in FIG. 9B. At the recessed position, the sensor face 118 separates from the ball of the finger F. In a configuration without the motion switch 142 being provided, in response to detection of contact of the ball of the finger F with the sensor face 118, the image sensor 108 and the sensor cover 110 including the sensor face 118 move from the capturing position toward the recessed position with the rear end part thereof moving down.

Subsequently, the image sensor 108 and the sensor cover 110 including the sensor face 118 that have moved to the recessed position move and return from the recessed position to the capturing position with the rear end part moving up, as illustrated in FIG. 9C. At the capturing position after the return, the sensor face 118 again comes into contact with the ball of the finger F.

Note that the CPU 166 of the fingerprint reading device 10 can use various triggers as a trigger for the switching from moving down to moving up of the rear end part of the image sensor 108 and the sensor cover 110. For example, when the rear end part of the image sensor 108 and the sensor cover 110 move down and separation of the sensor face 118 from the finger F is detected, the CPU 166 can use this as a trigger and drive the sensor drive unit 114 so as to move up the rear end part of the image sensor 108 and the sensor cover 110. That is, in response to detection of separation of the finger F from the sensor face 118 moving from the capturing position toward the recessed position, the sensor drive unit 114 moves the image sensor 108 and the sensor cover 110 including the sensor face 118 toward the capturing position. The separation of the finger F from the sensor face 118 can be detected based on a change in an image captured by the image sensor 108, for example, or can be detected by a sensor that can detect contact such as a touch sensor provided on the sensor face 118.

Further, when the user uses the motion switch 142 to manually move the image sensor 108 and the sensor cover 110, the following configuration is possible. That is, such a configuration is possible in which another press of the motion switch 142 causes the image sensor 108 and the sensor cover 110 including the sensor face 118 moving from the capturing position toward the recessed position to change the moving direction and move from the recessed position toward the capturing position. In this case, for example, in response to detecting the separation of the sensor face 118 from the finger F, the CPU 166 of the fingerprint reading device 10 or the CPU 202 of the image processing apparatus 20 notifies the user that the sensor face 118 has separated from the finger F by using a notification light, a notification sound, a screen display, or the like, for example. This enables the user to know the timing to move up the image sensor 108 and the sensor cover 110 without requiring to move down the whole of the image sensor 108 and the sensor cover 110. The user who has been notified of the separation of the sensor face 118 from the finger F again presses the motion switch 142. Another press of the motion switch 142 causes the image sensor 108 and the sensor cover 110 including the sensor face 118 to move from the recessed position, which is the position where the sensor face 118 that has separated from the finger F, toward the capturing position.

As discussed above, in the present example embodiment, the sensor face 118 once separates from the ball of the finger F at the recessed position. Subsequently, the sensor face 118 again comes into contact with the ball of the finger F at the capturing position recovered from the recessed position. The sensor face 118 once separates from the ball of the finger F, which can reduce or even remove elastic deformation of the finger F generated at the first contact of the sensor face 118. In the present example embodiment, after elastic deformation of the finger F is reduced or even removed in such a way, the fingerprint of the finger F is captured and read, and a fingerprint image is acquired as described below. Therefore, according to the present example embodiment, even when reading a fingerprint of the finger F which is relatively soft and may be easily elastically deformed, it is possible to appropriately read the fingerprint and acquire a high quality fingerprint image. When a fingerprint is read after elastic deformation that has occurred in the finger F is reduced or the like, the read fingerprint as illustrated in FIG. 10C is substantially the same as the ideal fingerprint illustrated in FIG. 10A.

Further, in the present example embodiment, while the image sensor 108 and the sensor cover 110 move from the capturing position to the recessed position and then return to the imaging position, the light guiding parts 124 support the finger F. That is, meanwhile, the edge parts 128 and parts of the protrusion parts 126, which correspond to portions of the light guiding parts 124 located extending over the ends of the sensor face 118 support the finger F from the sensor face 118 side. Therefore, according to the present example embodiment, although the sensor face 118 once separates from the ball of the finger F, displacement of the finger F can be suppressed or even prevented, and therefore the fingerprint of the finger F can be read more appropriately, and a higher quality fingerprint image can be acquired.

Japanese Patent Application Laid-Open No. 2005-182474 discloses a configuration in which, in response to detection of a finger being placed on the placement portion, a fingerprint sensor is moved up to the placement portion by a motor. In such a configuration, since the fingerprint sensor is located at a move-down position separated from the placement portion at time other than the time of reading a fingerprint, it is difficult to secure air tightness inside the casing, and thus there is a problem of dust resistance. In contrast, in the present example embodiment, the image sensor 108 and the sensor cover 110 are normally positioned at the capturing position and seal the inside of the placement portion 102 and, at the time of reading a fingerprint, are caused to move from the capturing position to the recessed position and further move and return from the recessed position to the capturing position. As discussed above, in the present example embodiment, since the image sensor 108 and the sensor cover 110 normally seal the inside of the placement portion 102, good dust resistance can be secured.

Next, in a state where the ball of the finger F is again in contact with the sensor face 118 of the fingerprint reading device 10, the user may press the capture switch 144. In response to this press of the capture switch 144, a capture instruction signal is input to instruct the fingerprint reading device 10 of capturing.

In response to the capture instruction signal input by press of the capture switch 144, the CPU 166 of the fingerprint reading device 10 drives the image sensor 108 and turns on the side light sources 112. Thereby, the fingerprint reading device 10 captures and reads a fingerprint of the finger F by using the image sensor 108 and acquires a fingerprint image. After acquisition of a fingerprint image, the CPU 166 of the fingerprint reading device 10 turns off the side light sources 112.

Further, in response to acquiring a fingerprint image, the CPU 166 of the fingerprint reading device 10 transfers the image data of the acquired fingerprint image to the image processing apparatus 20 via the communication cable 30.

In the image processing apparatus 20 to which image data of a fingerprint image has been transferred, after temporarily storing the image data in the RAM 206 as the image memory, the CPU 202 performs predetermined image processing on image data. Furthermore, the CPU 202 of the image processing apparatus 20 displays the fingerprint image on the display 214. Further, the CPU 202 of the image processing apparatus 20 records the fingerprint image in the HDD 208 or the like in response to input of a recording instruction from the user or automatically.

Second Example Embodiment

A fingerprint reading device and a fingerprint reading method according to a second example embodiment of the present invention will be described by using FIG. 11 to FIG. 13. Note that the same components as those in the fingerprint reading device according to the first example embodiment described above are labeled with the same references, and the description thereof will be omitted or simplified.

The basic configuration of the fingerprint reading device according to the present example embodiment is substantially the same as the configuration of the fingerprint reading device 10 according to the first example embodiment described above. The fingerprint reading device according to the present example embodiment is different from the fingerprint reading device 10 according to the first example embodiment in the position where the image sensor 108 is attached to the casing 106 and in a feature in which the image sensor 108 is supported and moved down and up by the sensor drive unit 114.

The specific configuration of the fingerprint reading device according to the present example embodiment will be described below by using FIG. 11 and FIG. 12. FIG. 11 is a plan view illustrating the fingerprint reading device according to the present example embodiment, which illustrates a plane viewed from the front face side out of the front face and the back face of the fingerprint reading device. FIG. 12 is a longitudinal sectional view illustrating the fingerprint reading device according to the present example embodiment, which illustrates a longitudinal sectional view taken along a line A-A of FIG. 11.

Figure 11:
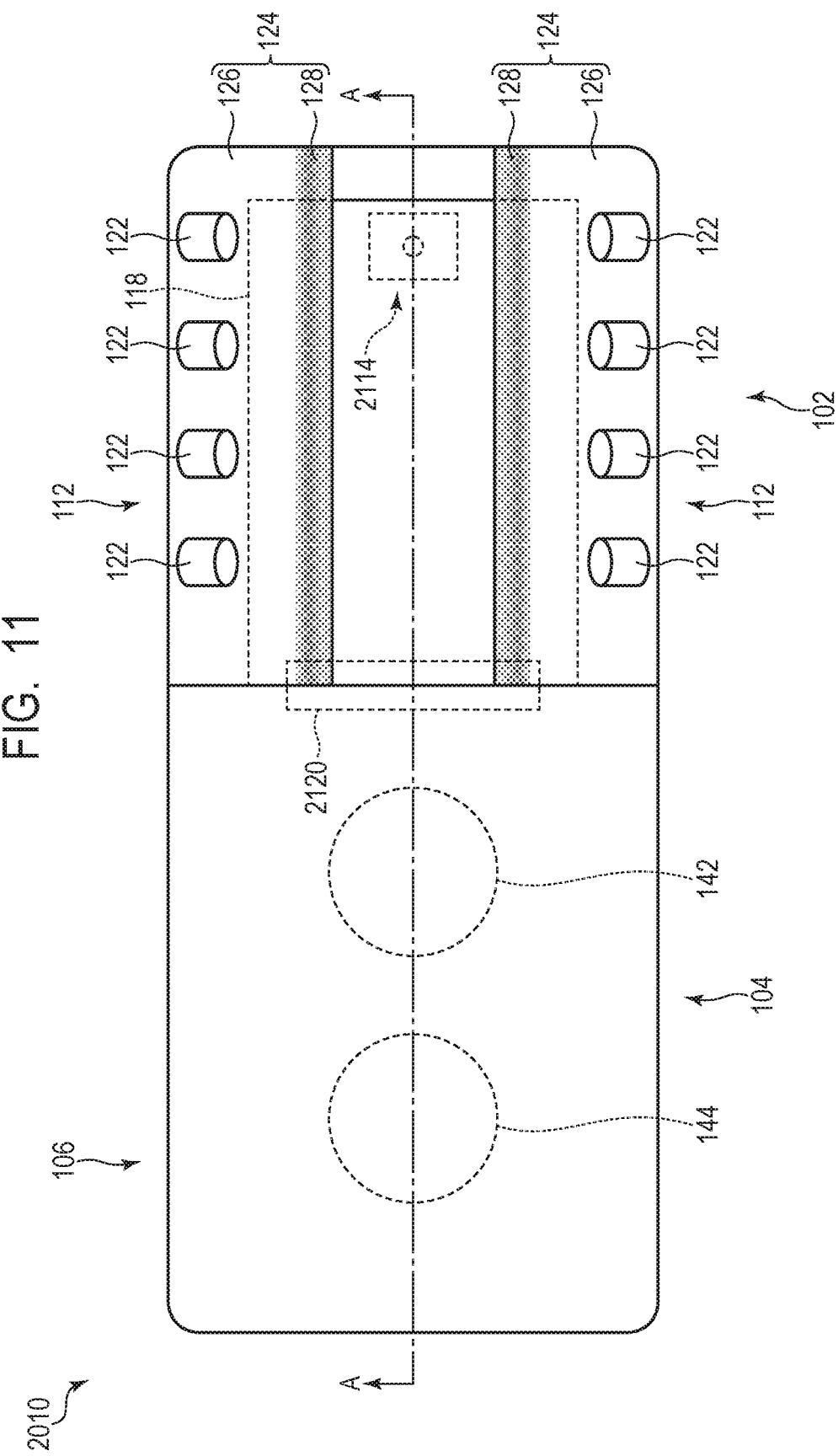
FIG. 11 is a plan view illustrating a fingerprint reading device according to a second example embodiment of the present invention.
Figure 12:
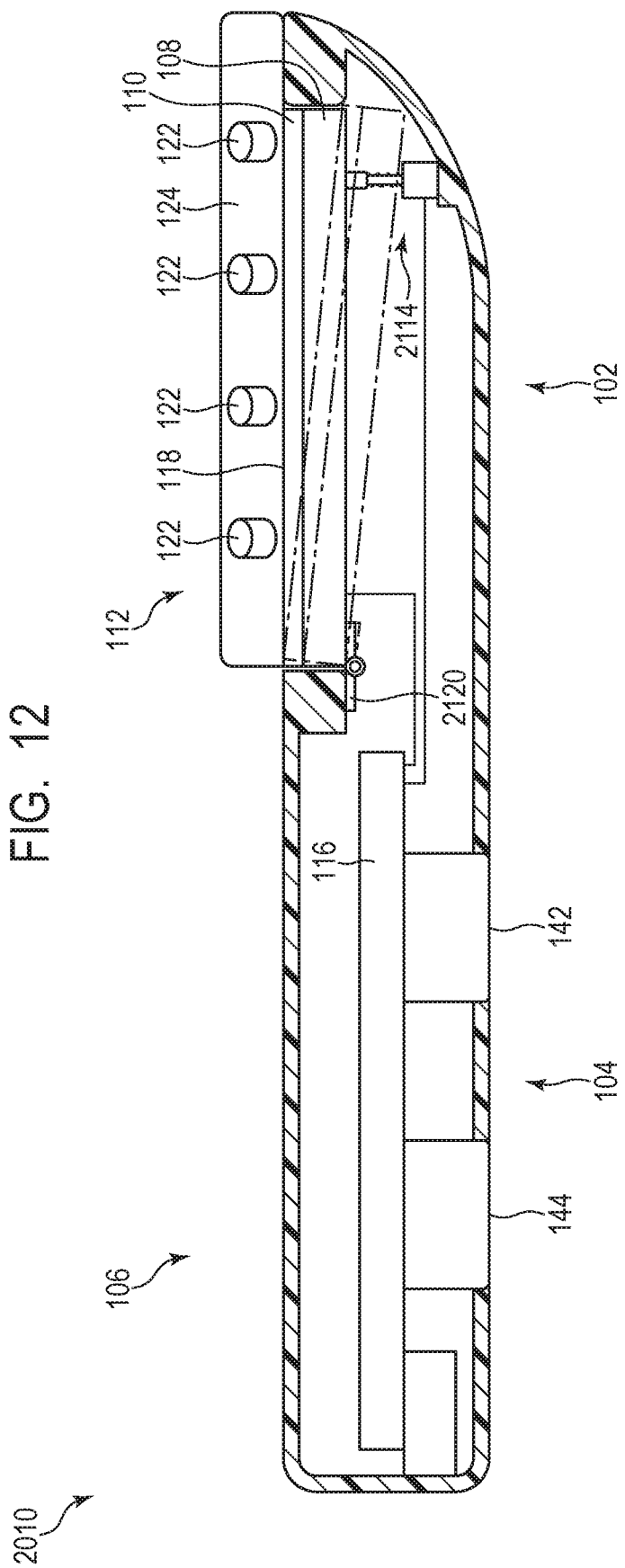
FIG. 12 is a longitudinal sectional view illustrating the fingerprint reading device according to the second example embodiment of the present invention.

As illustrated in FIG. 11 and FIG. 12, in a fingerprint reading device 2010 according to the present example embodiment, unlike the first example embodiment, the rear end part of the image sensor 108 is attached to a top plate front end of the holding portion 104 in the casing 106 via a hinge part 2120. The hinge part 2120 includes a rocking shaft extending in the width direction of the placement portion 102 in the casing 106.

The image sensor 108 and the sensor cover 110 including the sensor face 118 are provided so as to be swing about a rocking shaft of the hinge part 2120 located at the rear side end of the placement portion 102 as a fulcrum. This enables the image sensor 108 and the sensor cover 110 including the sensor face 118 to move between a capturing position, which is the first position, and a recessed position, which is the second position, located inside the casing 106 deeper than the capturing position.

At the capturing position, the image sensor 108 and the sensor cover 110 are arranged such that the sensor face 118 of the sensor cover 110 is orthogonal to the perpendicular direction of the placement portion 102 as with the first example embodiment. The image sensor 108 and the sensor cover 110 positioned at the capturing position seal the inside of the placement portion 102 as with the first example embodiment. On the other hand, at the recessed position, in the present example embodiment, unlike the first example embodiment, the image sensor 108 and the sensor cover 110 are arranged such that the sensor face 118 of the sensor cover 110 is inclined to face the frontward oblique upper direction of the placement portion 102.

The image sensor 108 and the sensor cover 110 including the sensor face 118 are driven by a sensor drive unit 2114 similar to the sensor drive unit 114 according to the first example embodiment and move between the capturing position and the recessed position.

In FIG. 12, the image sensor 108 and the sensor cover 110 at the capturing position are illustrated by the solid line, and the image sensor 108 and the sensor cover 110 at the recessed position are illustrated by the one-dot-chain line. As illustrated, the sensor face 118 of the sensor cover 110 at the capturing position is orthogonal to the perpendicular direction of the placement portion 102 and forms a flat face with the surface of the holding portion 104 with substantially no step in a similar manner to the first example embodiment. On the other hand, unlike the first example embodiment, the sensor face 118 of the sensor cover 110 at the recessed position is inclined so as to enter the inside of the casing 106 in the direction from the rear side to the front side of the placement portion 102.

The fingerprint reading device 2010 according to the present example embodiment has the sensor drive unit 2114 instead of the sensor drive unit 114 according to the first example embodiment. The sensor drive unit 2114 is provided under the front end part of the image sensor 108 inside the casing 106 of the placement portion 102. The sensor drive unit 2114 has the same drive mechanism as that of the sensor drive unit 114 according to the first example embodiment.

The sensor drive unit 2114 drives the front end part of the image sensor 108, which is attached to the casing 106 so as to be able to swing, to move up and down and causes the image sensor 108 and the sensor cover 110 including the sensor face 118 to swing and move.

Specifically, the sensor drive unit 2114 causes the front end part of the image sensor 108 positioned at the capturing position to move down and causes the image sensor 108 and the sensor cover 110 including the sensor face 118 to swing and move from the capturing position to the recessed position. Further, the sensor drive unit 2114 causes the front end part of the image sensor 108 positioned at the recessed position to move up and causes the image sensor 108 and the sensor cover 110 including the sensor face 118 to swing and move from the recessed position to the capturing position. In such a way, the sensor drive unit 2114 causes the image sensor 108 and the sensor cover 110 including the sensor face 118 to move from the capturing position to the recessed position and further move and return from the recessed position to the capturing position.

The configuration of the sensor drive unit 2114 is not limited to a particular configuration as with the sensor drive unit 114 according to the first example embodiment as long as it can move down and up the front end part of the image sensor 108. For example, the sensor drive unit 2114 may have a solenoid-type configuration in which a solenoid is used as an actuator as with the sensor drive unit 114 according to the first example embodiment.

Next, the operation of the fingerprint reading device 2010 according to the present example embodiment will be further described by using FIG. 13A to FIG. 13C. FIG. 13A to FIG. 13C are schematic diagrams illustrating the operation of the fingerprint reading device 2010 according to the present example embodiment. FIG. 13A to FIG. 13C illustrate the positional relationship of the finger F with the image sensor 108 and the sensor cover 110 while the finger F comes into contact with the sensor face 118 and then a fingerprint is captured. For simplified illustration, the side light sources 112 are omitted in FIG. 13A to FIG. 13C.

First, in a similar manner to the first example embodiment, in a state where the image sensor 108 and the sensor cover 110 including the sensor face 118 are positioned at the capturing position, the user causes the ball of the finger F of the subject to come into contact with the sensor face 118 of the fingerprint reading device 2010, as illustrated in FIG. 13A. In a state where the ball of the finger F is in contact with the sensor face 118, in a similar manner to the first example embodiment, the edge part 128 and a part of the protrusion part 126 in contact with the surface of the finger F on the sensor face 118 side support the finger F in contact with the sensor face 118.

Subsequently, in a state where the ball of the finger F is in contact with the sensor face 118, the user presses the motion switch 142 in a similar manner to the first example embodiment. With the motion switch 142 being pressed, a drive instruction signal is input to instruct the fingerprint reading device 2010 to drive the image sensor 108 and the sensor cover 110.

The CPU 166 of the fingerprint reading device 2010 drives the sensor drive unit 2114 in response to the drive instruction signal input by press of the motion switch 142 and drives the image sensor 108 and the sensor cover 110 including the sensor face 118. Thereby, the image sensor 108 and the sensor cover 110 including the sensor face 118 swing about a rocking shaft of the hinge part 2120 attached to the casing 106 of the rear end part of the image sensor 108 as a fulcrum.

Note that, also in the present example embodiment, in a configuration without the motion switch 142 being provided in a similar manner to the first example embodiment. In this case, in response to detection of contact of the ball of the finger F with the sensor face 118, the drive instruction signal is input, and the image sensor 108 and the sensor cover 110 are driven by the sensor drive unit 2114 in the same manner as described above.

The image sensor 108 and the sensor cover 110 including the sensor face 118 that start swinging first move from the capturing position to the recessed position with the front end part thereof moving down, as illustrated in FIG. 13B. At the recessed position, the sensor face 118 separates from the ball of the finger F. In a configuration without the motion switch 142 being provided, in response to detection of contact of the ball of the finger F with the sensor face 118, the image sensor 108 and the sensor cover 110 move from the capturing position toward the recessed position with the front end part thereof moving down.

Subsequently, the image sensor 108 and the sensor cover 110 including the sensor face 118 that have moved to the recessed position move and return from the recessed position to the capturing position with the front end part moving up, as illustrated in FIG. 13C. At the capturing position after the return, the sensor face 118 again comes into contact with the ball of the finger F.

Note that the CPU 166 of the fingerprint reading device 2010 can use various triggers as a trigger for the switching from moving down to moving up of the front end part of the image sensor 108 and the sensor cover 110. For example, when the front end part of the image sensor 108 and the sensor cover 110 move down and separation of the sensor face 118 from the finger F is detected, the CPU 166 can use this as a trigger and drive the sensor drive unit 2114 to move up the front end part of the image sensor 108 and the sensor cover 110. That is, in response to detection of separation of the finger F from the sensor face 118 moving from the capturing position toward the recessed position, the sensor drive unit 2114 moves the image sensor 108 and the sensor cover 110 including the sensor face 118 toward the capturing position. The separation of the finger F from the sensor face 118 can be detected in a similar manner to the first example embodiment.

Further, the present example embodiment may be configured such that, in a similar manner to the first example embodiment, another press of the motion switch 142 causes the image sensor 108 and the sensor cover 110 including the sensor face 118 moving from the capturing position toward the recessed position to change the moving direction and move from the recessed position toward the capturing position.

As discussed above, also in the present example embodiment, the sensor face 118 once separates from the ball of the finger F at the recessed position. Subsequently, the sensor face 118 again comes into contact with the ball of the finger F at the capturing position recovered from the recessed position. Thereby, also in the present example embodiment, elastic deformation of the finger F generated at the first contact to the sensor face 118 can be reduced or even removed. Therefore, according to the present example embodiment, even when reading a fingerprint of the finger F which is relatively soft and may be easily elastically deformed, it is possible to appropriately read the fingerprint and acquire a high quality fingerprint image.

Further, in the present example embodiment, while the image sensor 108 and the sensor cover 110 move from the capturing position to the recessed position and then return to the capturing position, the edge parts 128 and parts of the protrusion parts 126 in the light guiding parts 124 support the finger F from the sensor face 118 side. Therefore, according to the present example embodiment, although the sensor face 118 once separates from the ball of the finger F, displacement of the finger F can be suppressed or even prevented, and therefore the fingerprint of the finger F can be read more appropriately, and a higher quality fingerprint image can be acquired.

Also in the present example embodiment, since the image sensor 108 and the sensor cover 110 normally seal the inside of the placement portion 102, good dust resistance can be secured in a similar manner to the first example embodiment.

Since the subsequent operation is the same as the first example embodiment, the description thereof will be omitted.

Note that, while the case where the front end part or the rear end part of the image sensor 108 is attached to the casing 106 via the hinge part 2120 has been described in the above first and second example embodiments, a case is not limited thereto. For example, one of the side end parts of the image sensor 108 may be attached so as to be able to swing to one of the side parts of the placement portion 102 in the casing 106 via a hinge part. In such a case, the hinge part includes a rocking shaft extending in the front-rear direction of the placement portion 102 in the casing 106, for example. Further, in such a case, a sensor drive unit that drives the other side end part of the image sensor 108 to move up and down, which is similar to the sensor drive unit 114, may be provided inside the placement portion 102.

Third Example Embodiment

A fingerprint reading device and a fingerprint reading method according to a third example embodiment of the present invention will be described by using FIG. 14 to FIG. 17. Note that the same components as those in the fingerprint reading device and the fingerprint reading method according to the first and second example embodiments described above are labeled with the same references, and the description thereof will be omitted or simplified.

The basic configuration of the fingerprint reading device according to the present example embodiment is substantially the same as the configuration of the fingerprint reading device 10 according to the first example embodiment described above. The fingerprint reading device according to the present example embodiment is different from the fingerprint reading device 10 according to the first example embodiment in a manner of motion of the image sensor 108 and the sensor cover 110.

Figure 15:
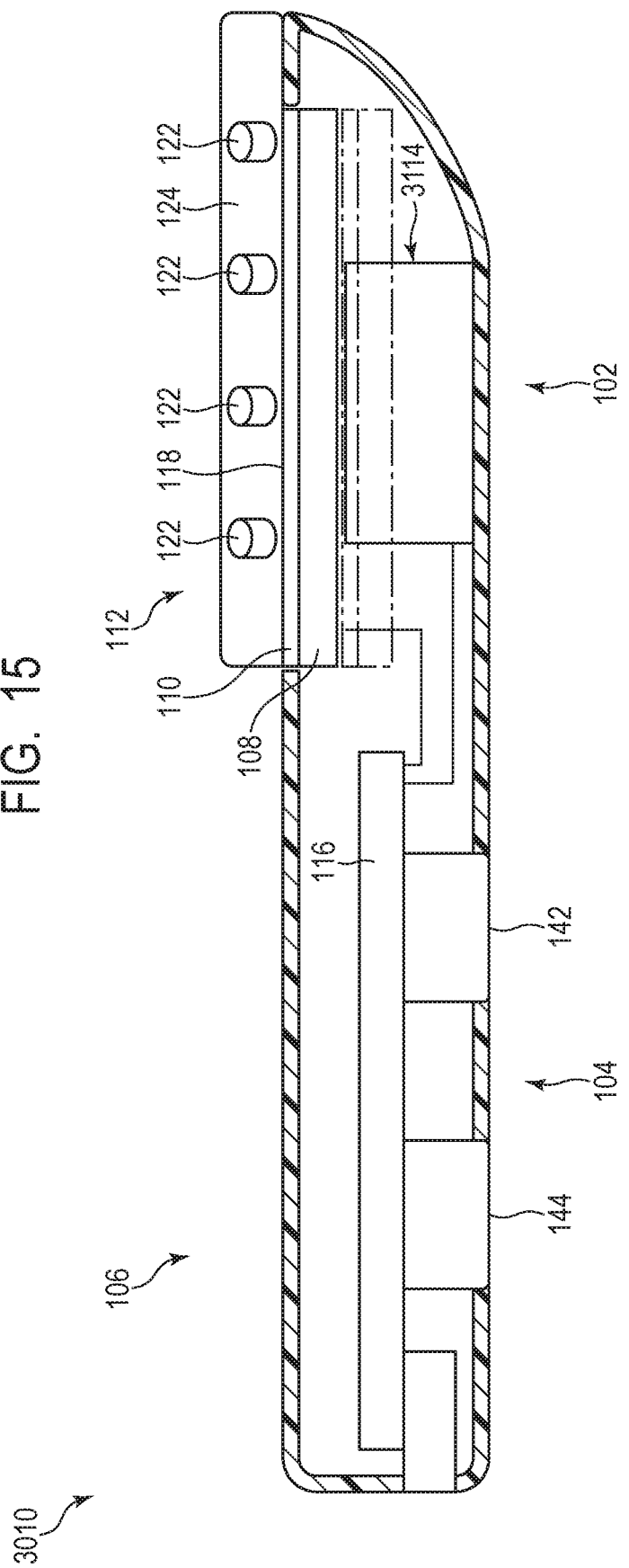
FIG. 15 is a longitudinal sectional view illustrating the fingerprint reading device according to the third example embodiment of the present invention.
Figure 16A:
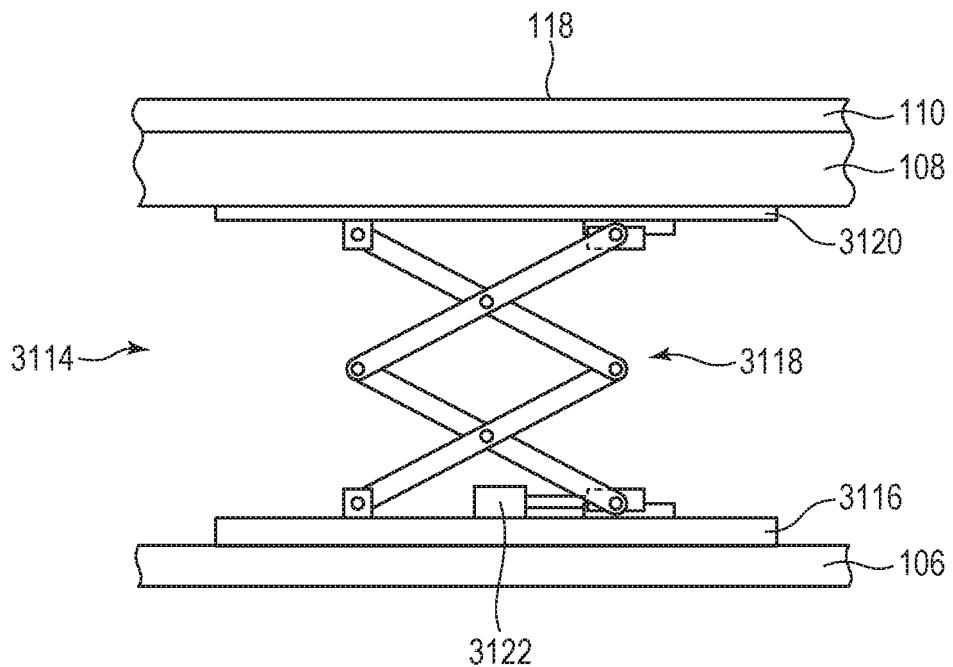
FIG. 16A is a schematic diagram illustrating an example of a sensor drive unit in the fingerprint reading device according to the third example embodiment of the present invention.
Figure 16B:
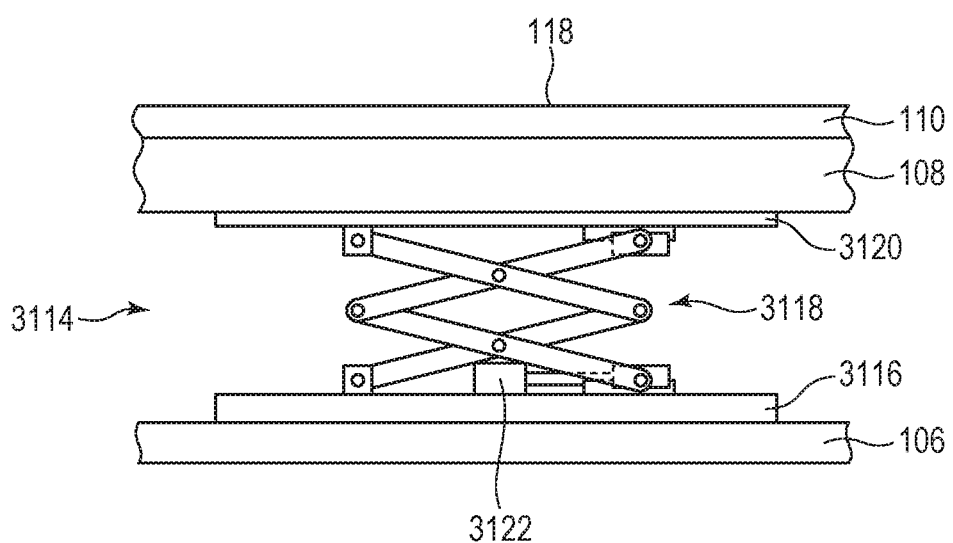
FIG. 16B is a schematic diagram illustrating an example of the sensor drive unit in the fingerprint reading device according to the third example embodiment of the present invention.

The specific configuration of the fingerprint reading device according to the present example embodiment will be described below by using FIG. 14 to FIG. 16B. FIG. 14 is a plan view illustrating the fingerprint reading device according to the present example embodiment, which illustrates a plane viewed from the front face side out of the front face and the back face of the fingerprint reading device. FIG. 15 is a longitudinal sectional view illustrating the fingerprint reading device according to the present example embodiment, which illustrates a longitudinal sectional view taken along a line A-A of FIG. 14. FIG. 16A and FIG. 16B are schematic diagram illustrating an example of a sensor drive unit in the fingerprint reading device according to the present example embodiment.

As illustrated in FIG. 14 and FIG. 15, in a fingerprint reading device 3010 according to the present example embodiment, unlike the first example embodiment, the image sensor 108 is attached to the bottom inside the casing 106 of the placement portion 102 via a sensor drive unit 3114.

The image sensor 108 and the sensor cover 110 including the sensor face 118 are able to parallelly shift in the perpendicular direction of the casing 106 via the sensor drive unit 3114. The direction in which the image sensor 108 and the sensor cover 110 are able to parallelly shift is the direction orthogonal to the sensor face 118. This enables the image sensor 108 and the sensor cover 110 including the sensor face 118 to move between a capturing position, which is the first position, and a recessed position, which is the second position, located inside the casing 106 deeper than the capturing position. In the present example embodiment, unlike the first example embodiment, also at the recessed position, the image sensor 108 and the sensor cover 110 are not inclined, and the sensor face 118 of the sensor cover 110 remains orthogonal to the perpendicular direction of the casing 106. Note that the image sensor 108 and the sensor cover 110 positioned at the capturing position seal the inside of the placement portion 102 in a similar manner to the first example embodiment.

The image sensor 108 and the sensor cover 110 including the sensor face 118 are driven by the sensor drive unit 3114 and move between the capturing position and the recessed position.

In FIG. 15, the image sensor 108 and the sensor cover 110 at the capturing position are illustrated by the solid line, and the image sensor 108 and the sensor cover 110 at the recessed position are illustrated by the one-dot-chain line. As illustrated, the sensor face 118 of the sensor cover 110 at the capturing position is orthogonal to the perpendicular direction of the placement portion 102 and forms a flat face with the surface of the holding portion 104 with substantially no step in a similar manner to the first example embodiment. On the other hand, the sensor face 118 of the sensor cover 110 at the recessed position is located inside the casing 106 deeper than when positioned at the capturing position and remains orthogonal to the perpendicular direction of the placement portion 102.

The fingerprint reading device 3010 according to the present example embodiment has the sensor drive unit 3114 instead of the sensor drive unit 114 according to the first example embodiment. The sensor drive unit 3114 is provided under the center part of the image sensor 108 in the casing 106 of the placement portion 102. The image sensor 108 is attached on the top of the sensor drive unit 3114.

The sensor drive unit 3114 drives the image sensor 18 attached on the top thereof to move down and up and parallelly shifts the image sensor 108 and the sensor cover 110.

Specifically, the sensor drive unit 3114 causes the entire image sensor 108 positioned at the capturing position to move down and thereby the image sensor 108 and the sensor cover 110 including the sensor face 118 to parallelly shift from the capturing position to the recessed position. Further, the sensor drive unit 3114 causes the entire image sensor 108 positioned at the recessed position to move up and thereby the image sensor 108 and the sensor cover 110 including the sensor face 118 to parallelly shift from the recessed position to the capturing position. In such a way, the sensor drive unit 3114 causes the image sensor 108 and the sensor cover 110 including the sensor face 118 to move from the capturing position to the recessed position and further move and return from the recessed position to the capturing position.

The configuration of the sensor drive unit 3114 is not limited to a particular configuration, and any configuration that can move down and up the entire image sensor 108 may be employed. For example, the sensor drive unit 3114 may have a pantograph-type configuration in which a pantograph mechanism is used. FIG. 16A and FIG. 16B illustrate one having a pantograph-type configuration as an example of the sensor drive unit 3114. FIG. 16A is a side view illustrating the pantograph-type sensor drive unit 3114 when the image sensor 108 is positioned at the capturing position. FIG. 16B is a side view illustrating the pantograph-type sensor drive unit 3114 when the image sensor 108 is positioned at the recessed position.

As illustrated in FIG. 16A and FIG. 16B, the pantograph-type sensor drive unit 3114 has a base 3116, a pantograph mechanism including pantograph arms 3118, and a support part 3120. Note that two pantograph arms 3118 are provided adjacently in parallel, for example. Further, the pantograph-type sensor drive unit 3114 has a drive mechanism 3122 that drives the pantograph arms 3118.

The base 3116 is provided on the bottom inside the casing 106 in the placement portion 102. The support part 3120 is provided above the base 3116 via the pantograph arms 3118. The drive mechanism 3122 is provided on the base 3116.

One end and the other end on the lower side of the pantograph arms 3118 are pivotally supported on the base 3116. One of the one end and the other end on the lower side of the pantograph arm 3118 is slidable along the base 3116. One end and the other end on the upper side of the pantograph arms 3118 are pivotally supported on the support part 3120. One of the one end and the other end on the upper side of the pantograph arm 3118 is slidable along the support part 3120.

The drive mechanism 3122 drives one end on the lower side of the pantograph arms 3118 to slide. The drive mechanism 3122 is not limited to a particular mechanism, and may be a mechanism that performs electrical slide driving or may be a mechanism that performs mechanical slide driving. For example, as the drive mechanism 3122, an electrical drive mechanism that drives one end on the lower side of the pantograph arms 3118 to slide by using a ball screw rotated by a drive motor, a solenoid, or the like can be used. Further, as the drive mechanism 3122, a mechanical drive mechanism that drives one end on the lower side of the pantograph arms 3118 to slide by using a manually operated lever or the like can be used, for example.

The pantograph arms 3118 expand and contract in the perpendicular direction of the casing 106 by one end on the lower side thereof being driven by the drive mechanism 3122 and sliding. That is, the pantograph arms 3118 expand by one end on the lower side thereof being driven by the drive mechanism 3122 and sliding so that one end on the lower side thereof approaches the other end. Further, the pantograph arms 3118 contract by one end on the lower side thereof being driven by the drive mechanism 3122 and sliding so that one end on the lower side thereof separates from the other end.

The image sensor 108 is attached to the support part 3120. The image sensor 108 and the sensor cover 110 are supported so that the sensor face 118 is orthogonal to the perpendicular direction of the casing 106.

As illustrated in FIG. 16A, in a state where the pantograph arms 3118 have expanded, the image sensor 108 and the sensor cover 110 including the sensor face 118 supported by the support part 3120 are positioned at the capturing position.

As illustrated in FIG. 16B, when the pantograph arms 3118 are transferred from the expansion state to the contraction state by the drive mechanism 3122, the image sensor 108 and the sensor cover 110 including the sensor face 118 supported by the support part 3120 move down from the capturing position. Thereby, the image sensor 108 and the sensor cover 110 including the sensor face 118 move to the recessed position.

Furthermore, when the pantograph arms 3118 are transferred from the contraction state to the expansion state by the drive mechanism 3122, the image sensor 108 and the sensor cover 110 including the sensor face 118 supported by the support part 3120 move and return from the recessed position to the capturing position.

In such a way, the pantograph-type sensor drive unit 3114 moves down and up the whole of the image sensor 108 and the sensor cover 110 by using the pantograph arms 3118. Thereby, the sensor drive unit 3114 causes the image sensor 108 and the sensor cover 110 to parallelly shift and thereby the image sensor 108 and the sensor cover 110 including the sensor face 118 to move between the capturing position and the recessed position.

As described above, a pantograph-type one having a pantograph mechanism can be used as the sensor drive unit 3114.

Next, the operation of the fingerprint reading device 3010 according to the present example embodiment will be further described by using FIG. 17A to FIG. 17C. FIG. 17A to FIG. 17C are schematic diagrams illustrating the operation of the fingerprint reading device 3010 according to the present example embodiment. FIG. 17A to FIG. 17C illustrate the positional relationship of the finger F with the image sensor 108 and the sensor cover 110 after the finger F comes into contact with the sensor face 118 and before a fingerprint is captured. For simplified illustration, the side light sources 112 are omitted in FIG. 17A to FIG. 17C.

First, in a similar manner to the first example embodiment, in a state where the image sensor 108 and the sensor cover 110 including the sensor face 118 are positioned at the capturing position, the user causes the ball of the finger F of a subject to come into contact with the sensor face 118 of the fingerprint reading device 3010, as illustrated in FIG. 17A. In a state where the ball of the finger F is in contact with the sensor face 118, in the same manner as the first example embodiment, the edge parts 128 and parts of the protrusion parts 126 in contact with the surface of the finger F on the sensor face 118 side support the finger F in contact with the sensor face 118 from the sensor face 118 side.

Next, in a state where the ball of the finger F is in contact with the sensor face 118, the user presses the motion switch 142 in the similar manner to the first example embodiment. With the motion switch 142 being pressed, a drive instruction signal is input to instruct the fingerprint reading device 3010 to drive the image sensor 108 and the sensor cover 110.

The CPU 166 of the fingerprint reading device 3010 drives the sensor drive unit 3114 in response to the drive instruction signal input by press of the motion switch 142 and drives the image sensor 108 and the sensor cover 110 including the sensor face 118. Thereby, the image sensor 108 and the sensor cover 110 including the sensor face 118 parallelly shift in the perpendicular direction of the casing 106.

Note that, also in the present example embodiment, a configuration without the motion switch 142 being provided is possible in a similar manner to the first example embodiment. In this case, in response to detection of contact of the ball of the finger F with the sensor face 118, the drive instruction signal is input, and the image sensor 108 and the sensor cover 110 are driven by the sensor drive unit 3114 in the same manner as described above.

The image sensor 108 and the sensor cover 110 including the sensor face 118 that starts parallelly shifting first move down as a whole and move from the capturing position to the recessed position, as illustrated in FIG. 17B. At the recessed position, the sensor face 118 separates from the ball of the finger F. In the configuration without the motion switch 142 being provided, in response to detection of the contact of the ball of the finger F with the sensor face 118, the image sensor 108 and the sensor cover 110 move down as a whole and move from the capturing position toward the recessed position.

Subsequently, the image sensor 108 and the sensor cover 110 including the sensor face 118 that have moved to the recessed position move up as a whole and move and return from the recessed position to the capturing position, as illustrated in FIG. 17C. At the capturing position after the return, the sensor face 118 again comes into contact with the ball of the finger F.

Note that the CPU 166 of the fingerprint reading device 3010 can use various triggers as a trigger for the switching from moving down to moving up of the whole of the image sensor 108 and the sensor cover 110. For example, when the whole of the image sensor 108 and the sensor cover 110 move down and separation of the sensor face 118 from the finger F is detected, the CPU 166 can use this detection as a trigger and drive the sensor drive unit 3114 so as to move up the whole of the image sensor 108 and the sensor cover 110. That is, in response to detection of separation of the finger F from the sensor face 118 moving from the capturing position toward the recessed position, the sensor drive unit 3114 moves the image sensor 108 and the sensor cover 110 including the sensor face 118 toward the capturing position. The separation of the finger F from the sensor face 118 can be detected in a similar manner to the first example embodiment.

Further, the present example embodiment can be also configured such that, in a similar manner to the first example embodiment, another press of the motion switch 142 causes the image sensor 108 and the sensor cover 110 including the sensor face 118 moving from the capturing position toward the recessed position to change the moving direction and move from the recessed position toward the capturing position.

As discussed above, also in the present example embodiment, the sensor face 118 once separates from the ball of the finger F at the recessed position. Subsequently, the sensor face 118 again comes into contact with the ball of the finger F at the capturing position recovered from the recessed position. Thereby, also in the present example embodiment, elastic deformation of the finger F generated at the first contact to the sensor face 118 can be reduced or even removed. Therefore, according to the present example embodiment, even when reading a fingerprint of the finger F which is relatively soft and may be easily elastically deformed, it is possible to appropriately read the fingerprint and acquire a high quality fingerprint image.

Further, in the present example embodiment, while the image sensor 108 and the sensor cover 110 move from the capturing position to the recessed position and then return to the imaging position, the edge parts 128 and parts of the protrusion parts 126 in the light guiding parts 124 support the finger F from the sensor face 118 side. Therefore, according to the present example embodiment, although the sensor face 118 once separates from the ball of the finger F, displacement of the finger F can be suppressed, and therefore the fingerprint of the finger F can be read more appropriately, and a higher quality fingerprint image can be acquired.

Also in the present example embodiment, since the image sensor 108 and the sensor cover 110 normally seal the inside of the placement portion 102, good dust resistance can be secured in a similar manner to the first example embodiment.

Since the subsequent operation is the same as the first example embodiment, the description thereof will be omitted.

Fourth Example Embodiment

A fingerprint reading device and a fingerprint reading method according to a fourth example embodiment of the present invention will be described by using FIG. 18. Note that the same components as those in the fingerprint reading device and the fingerprint reading method according to the first to third example embodiments described above are labeled with the same references, and the description thereof will be omitted or simplified.

The basic configuration of the fingerprint reading device according to the present example embodiment is substantially the same as the configuration of the fingerprint reading device 10 according to the first example embodiment described above. The fingerprint reading device according to the present example embodiment is different from the fingerprint reading device 10 according to the first example embodiment in the shape of light guiding parts in the side light sources 112.

The specific configuration of the fingerprint reading device according to the present example embodiment will be described below by using FIG. 18. FIG. 18 is a plan view illustrating the fingerprint reading device according to the present example embodiment, which illustrates a plane corresponding to the plane of the fingerprint reading device 10 according to the first example embodiment illustrated in FIG. 2.

Figure 18:
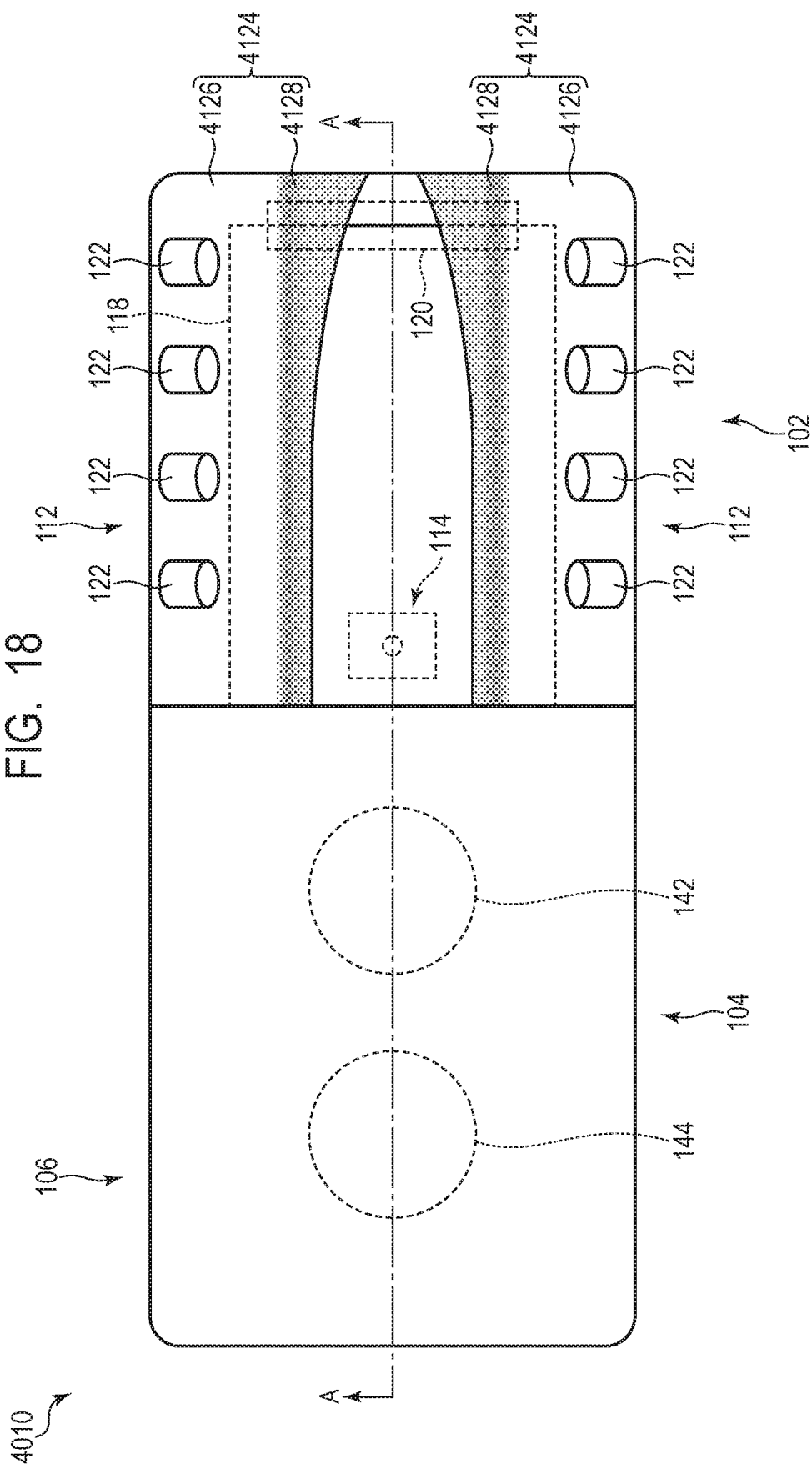
FIG. 18 is a plan view illustrating a fingerprint reading device according to a fourth example embodiment of the present invention.

As illustrated in FIG. 18, in a fingerprint reading device 4010 according to the present example embodiment, each of the pair of side light sources 112 has a light guiding part 4124 instead of the light guiding part 124 according to the first example embodiment. Note that the light-transmitting material of the light guiding parts 4124 is the same as that of the light guiding parts 124 according to the first example embodiment.

The light guiding part 4124 in each side light source 112 is formed extending in the front-rear direction of the placement portion 102 in a similar manner to the light guiding part 124 according to the first example embodiment. The light guiding part 4124 has a ridge-like protrusion part 4126 and a skirt-like edge part 4128. The protrusion part 4126 is the same as the protrusion part 126 according to the first example embodiment.

The edge part 4128 is formed in a skirt-like manner integrally with the protrusion part 4126 so as to extend on the sensor face 118 side of the protrusion part 4126 continuously from the protrusion part 4126 on the sensor face 118 side in a similar manner to the edge part 128 according to the first example embodiment. The edge part 4128 has a lower height in the perpendicular direction of the placement portion 102 than the protrusion part 4126, and the height thereof gradually decreases toward the sensor face 118 side. A part of the protrusion part 4126 on the edge part 4128 side and the edge part 4128 are located protruding over the end of the sensor face 118 in the same manner as in the first example embodiment.

Furthermore, unlike the edge part 128 according to the first example embodiment, the edge part 4128 has a portion whose protruding width, which is a width located over the end of the sensor face 118, is not constant. Specifically, in the front side part of the placement portion 102, the edge part 4128 has an increasing protruding width thereof toward the front side of the placement portion 102 in the front-rear direction of the placement portion 102. Thus, the spacing between the edge part 4128 of one of the side light sources 112 and the edge part 4128 of the other side light source 112 is narrower toward the front side of the placement portion 102 in the front-rear direction of the placement portion 102.

As discussed above, in the fingerprint reading device 4010 according to the present example embodiment, with a portion having wider protruding widths of the edge parts 4128 in the front side part of the placement portion 102 as described above, it is possible to more tightly support a finger whose fingerprint is to be read from the sensor face 118 side. Thus, according to the present example embodiment, it is possible to further ensure to suppress displacement of a finger whose fingerprint is to be read. Further, the portion having a wider protruding width of the edge part 4128 is located in the front side part of the placement portion 102 and thus does not prevent capturing of a fingerprint performed by the image sensor 108. Therefore, according to the present example embodiment, the fingerprint can be read more appropriately, and a higher quality fingerprint image can be acquired.

Further, the tip part of a finger has a more feature amount of a fingerprint than the root part of the finger. Thus, in the present example embodiment, as illustrated in FIG. 18, although the edge parts 4128 corresponding to the root part of a finger is present, since a part corresponding to the tip part of the finger is opened, the tip part of the finger is able to come into contact with the sensor face 118, and a fingerprint image can be acquired.

Note that, while a case where the light guiding parts 4124 are provided instead of the light guiding parts 124 in the first example embodiment has been described above, the light guiding parts 4124 may be provided instead of the light guiding part 124 also in the second and third example embodiments.

Fifth Example Embodiment

A fingerprint reading device and a fingerprint reading method according to a fifth example embodiment of the present invention will be described by using FIG. 19. Note that the same components as those in the fingerprint reading device and the fingerprint reading method according to the first to fourth example embodiments described above are labeled with the same references, and the description thereof will be omitted or simplified.

The basic configuration of the fingerprint reading device according to the present example embodiment is substantially the same as the configuration of the fingerprint reading device 10 according to the first example embodiment described above. The fingerprint reading device according to the present example embodiment is different from the fingerprint reading device 10 according to the first example embodiment in the shape of light guiding parts in the side light sources 112.

The specific configuration of the fingerprint reading device according to the present example embodiment will be described below by using FIG. 19. FIG. 19 is a plan view illustrating the fingerprint reading device according to the present example embodiment, which illustrates a plane corresponding to the plane of the fingerprint reading device 10 according to the first example embodiment illustrated in FIG. 2.

Figure 19:
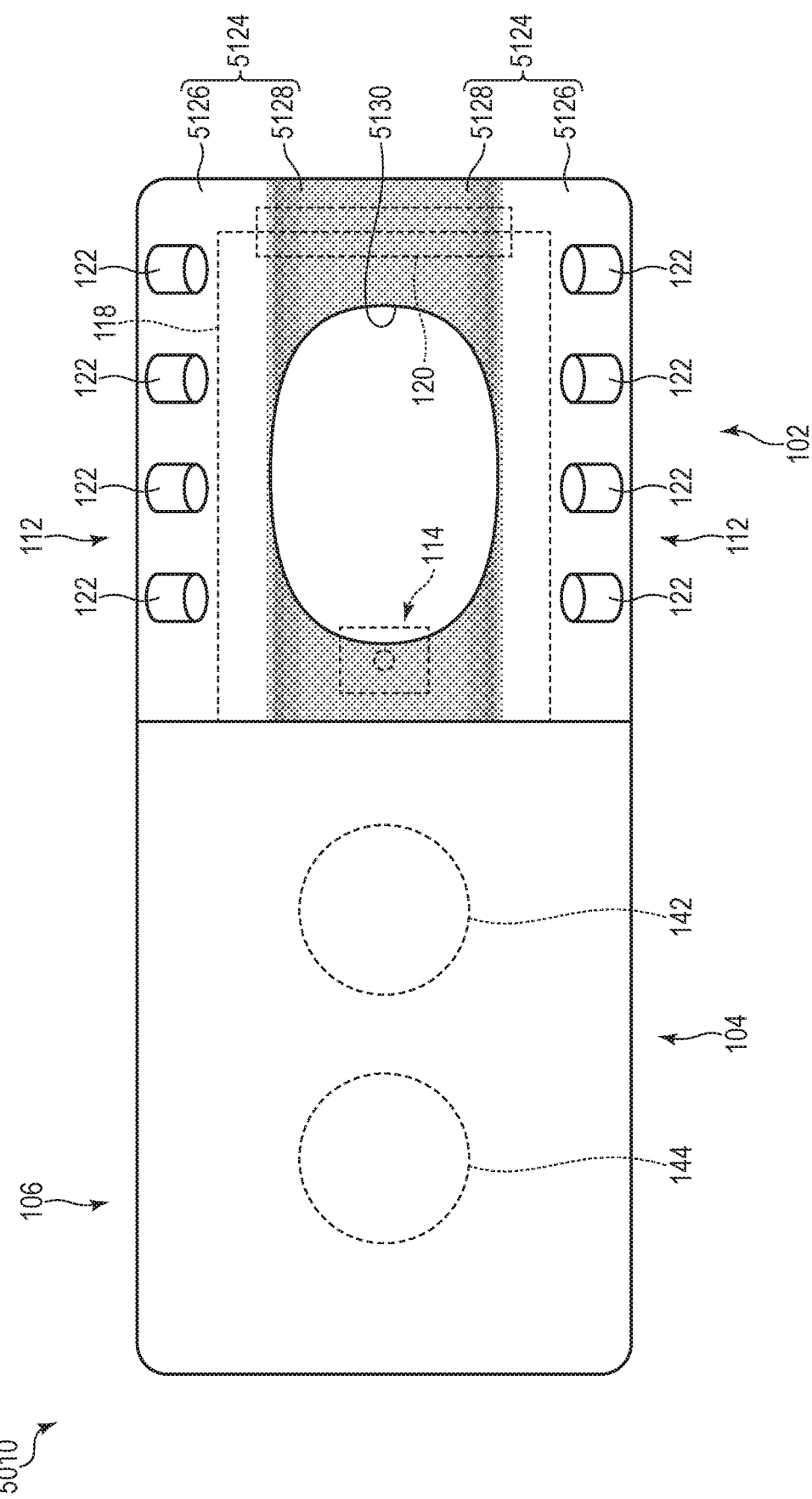
FIG. 19 is a plan view illustrating a fingerprint reading device according to a fifth example embodiment of the present invention.

As illustrated in FIG. 19, in a fingerprint reading device 5010 according to the present example embodiment, each of the pair of side light sources 112 has a light guiding part 5124 instead of the light guiding part 124 according to the first example embodiment. Note that the light-transmitting material of the light guiding parts 5124 is the same as that of the light guiding parts 124 according to the first example embodiment.

The light guiding part 5124 in each side light source 112 is formed extending in the front-rear direction of the placement portion 102 in a similar manner to the light guiding part 124 according to the first example embodiment. The light guiding part 5124 has a ridge-like protrusion part 5126 and a skirt-like edge part 5128. The protrusion part 5126 is the same as the protrusion part 126 according to the first example embodiment.

The edge part 5128 is formed in a skirt-like manner integrally with the protrusion part 5126 so as to extend on the sensor face 118 side of the protrusion part 5126 continuously from the protrusion part 5126 on the sensor face 118 side in a similar manner to the edge part 128 according to the first example embodiment. The edge part 5128 has a lower height in the perpendicular direction of the placement portion 102 than the protrusion part 5126, and the height thereof gradually decreases toward the sensor face 118 side. A part of the protrusion part 5126 on the edge part 5128 side and the edge part 5128 are located protruding over the end of the sensor face 118 in the same manner as in the first example embodiment.

Furthermore, in the present example embodiment, the edge part 5128 of one of the side light sources 112 and the edge part 5128 of the other side light source 112 are formed to extend across the sensor face 118 and be continuous to each other across the sensor face 118. The same light shielding parts 130 as those in the first example embodiment are formed on the underside of the edge parts 5128 extending over the sensor face 118.

An opening 5130 that exposes the sensor face 118 is formed in the center part of the edge parts 5128 extending across the sensor face 118. The opening 5130 is formed such that a part of the sensor face 118 of the shape and the area by which a fingerprint can be read is exposed when the image sensor 108 and the sensor cover 110 are positioned at the capturing position. The planar shape of the opening 5130 is not particularly limited but may be an ellipse or a shape of a fingertip, for example.

As discussed above, in the fingerprint reading device 5010 according to the present example embodiment, with a portion other than the opening 5130 of the edge parts 5128 extending across the sensor face 118 as described above, it is possible to more tightly support a finger whose fingerprint is to be read from the sensor face 118 side. Thus, according to the present example embodiment, it is possible to further ensure to suppress displacement of a finger whose fingerprint is to be read. Further, since the image sensor 108 is able to capture a fingerprint through the opening 5130, capturing of a fingerprint performed by the image sensor 108 is not prevented. Therefore, according to the present example embodiment, the fingerprint can be read more appropriately, and a higher quality fingerprint image can be acquired.

Further, also in the present example embodiment, as illustrated in FIG. 19, although the edge parts 5128 corresponding to the root part of a finger is present, since a part corresponding to the tip part of a finger having a large feature amount of the fingerprint is opened, the tip part of the finger is able to come into contact with the sensor face 118, and a fingerprint image can be acquired.

Note that, while a case where the light guiding parts 5124 are provided instead of the light guiding parts 124 in the first example embodiment has been described above, the light guiding parts 5124 may be provided instead of the light guiding part 124 also in the second and third example embodiments.

Sixth Example Embodiment

A fingerprint reading device and a fingerprint reading method according to a sixth example embodiment of the present invention will be described by using FIG. 20. Note that the same components as those in the fingerprint reading device and the fingerprint reading method according to the first to fifth example embodiments described above are labeled with the same references, and the description thereof will be omitted or simplified.

While the case where a newborn, an infant, or a young child is a subject whose fingerprint is to be read has been described in the above first to fifth example embodiments, a subject is not limited to a newborn, an infant, and a young child. The fingerprint reading device can be applied to persons of any age group as a subject in addition to a newborn, an infant, and a young child.

In the present example embodiment, a case where the fingerprint reading device is applied not only to a newborn, an infant, and a young child but also to persons other than a newborn, an infant, and a young child as a subject will be described. Note that persons other than a newborn, an infant, and a young child include an adult and a minor other than a newborn, an infant, and a young child. In the following description, a newborn, an infant, and a young child are denoted as "newborn or the like", and persons other than a newborn, an infant, and a young child are denoted as "adult or the like".

The basic configuration of the fingerprint reading device according to the present example embodiment that is applied to a newborn or the like and an adult or the like as a subject is substantially the same as the configuration of the fingerprint reading device 10 according to the first example embodiment. Since the fingerprint reading device according to the present example embodiment is different from the fingerprint reading device 10 according to the first example embodiment in the shape of light guiding parts in the side light sources 112 because an adult or the like may also be a subject.

The specific configuration of the fingerprint reading device according to the present example embodiment will be described below by using FIG. 20. FIG. 20 is a transverse sectional view illustrating a fingerprint reading device according to the present example embodiment, which illustrates a horizontal cross section corresponding to the horizontal cross section of the fingerprint reading device 10 according to the first example embodiment illustrated in FIG. 4. Note that, in FIG. 20, the light guiding parts 124 according to the first example embodiment are illustrated by one-dot-chain lines for the purpose of comparison.

Figure 20:
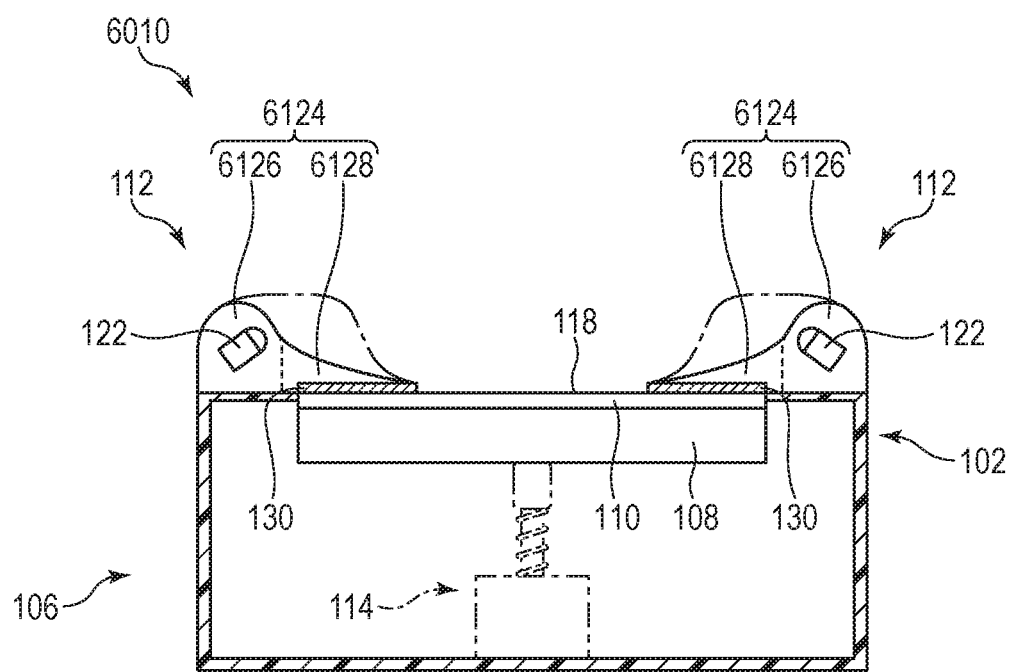
FIG. 20 is a transverse sectional view illustrating a fingerprint reading device according to a sixth example embodiment of the present invention.

As illustrated in FIG. 20, in a fingerprint reading device 6010 according to the present example embodiment, each of the pair of side light sources 112 has a light guiding part 6124 instead of the light guiding part 124 according to the first example embodiment. Note that the light-transmitting material of the light guiding parts 6124 is the same as that of the light guiding parts 124 according to the first example embodiment.

The light guiding part 6124 in each of the side light sources 112 is formed extending in the front-rear direction of the placement portion 102 in a similar manner to the light guiding part 124 according to the first example embodiment. The light guiding part 6124 has a ridge-like protrusion part 6126 and a skirt-like edge part 6128.

The protrusion part 6126 is formed in a ridge-like manner so as to cover the plurality of near-infrared LEDs 122 and protrude above the top face of the casing 106 in a similar manner to the protrusion part 126 according to the first example embodiment. Unlike the protrusion part 126 according to the first example embodiment, however, the protrusion part 6126 is formed to neither protrude over the end of the sensor face 118 nor be located over the end of the sensor face 118.

The edge part 6128 is formed in a skirt-like manner integrally with the protrusion part 6126 so as to extend on the sensor face 118 side of the protrusion part 6126 continuously from the protrusion part 6126 on the sensor face 118 side in a similar manner to the edge part 128 according to the first example embodiment. The edge part 6128 has a lower height in the perpendicular direction of the placement portion 102 than the protrusion part 6126, and the height thereof gradually decreases toward the sensor face 118 side. In the present example embodiment, a part of the edge part 6128 is located protruding over the end of the sensor face 118.

Each light shielding part 130 is provided on the underside of the sensor face 118 of a part of the edge parts 6128, which is a portion located protruding over the end of the sensor face 118 of the light guiding part 6124 in a similar manner to the first example embodiment.

Note that the protruding width, which is a width located over the end of the sensor face 118 that is a protruding part of the edge part 6128 can be appropriately set to be able to read not only a finger of a newborn or the like but also a fingerprint of an adult or the like.

As discussed above, in the present example embodiment, the protrusion part 6126 does not protrude over the end of the sensor face 118, and only a part of the edge part 6128 of the light guiding part 6124 is protruded and located over the end of the sensor face 118. Thus, in the present example embodiment, since a wider space is secured above the sensor face 118 compared to the first example embodiment, a finger of an adult or the like that is larger than a finger of a newborn or the like can come into contact with the sensor face 118. Thereby, in the present example embodiment, not only a fingerprint of a newborn or the like but also a fingerprint of an adult or the like can be read in a similar manner to the first example embodiment.

Note that, when a fingerprint of an adult or the like as a subject is read, the subject of the adult or the like is able to operate the fingerprint reading device 6010 by himself/ herself to have the fingerprint of his/her own finger read. In such a case, the subject is able to cause the ball of a finger whose fingerprint is to be captured to come into contact with the sensor face 118 of the sensor cover 110 while holding the holding portion 104 by a hand opposite to the hand including a finger whose fingerprint is to be captured. The subject is able to hold the holding portion 104 from the sides such that, out of fingers holding the holding portion 104, the thumb is located on the top plate side of the casing 106 and four fingers of the hand other than the thumb are located on the bottom plate side of the casing 106, for example.

The subject of an adult or the like holding the holding portion 104 is able to press the motion switch 142 and the capture switch 144 by using any of the four fingers located on the bottom plate side of the casing 106 out of the fingers of the hand holding the holding portion 104 while holding the holding portion 104. By a subject operating the motion switch 142 and the capture switch 144 by himself/herself, a fingerprint of the subject can be read in a similar manner to the first example embodiment. Also when a fingerprint of a finger of an adult or the like is read, the finger may be significantly elastically deformed due to influence of a moisture state, a high water-retention capability, a high moisture percentage, or the like, for example. According to the present example embodiment, also when a fingerprint of a finger of an adult or the like is read, since the fingerprint is read after elastic deformation occurring in the finger is reduced or even removed in a similar manner to the first example embodiment, the fingerprint can be read more appropriately, and a higher quality fingerprint image can be acquired.

However, when a fingerprint of a newborn or the like as a subject is read, the fingerprint of the subject can be read in the same manner as the first example embodiment.

Note that, while a case where the light guiding parts 6124 are provided instead of the light guiding parts 124 in the first example embodiment has been described above, the light guiding parts 6124 may be provided instead of the light guiding part 124 also in the second and third example embodiments.

Further, also in the fourth and fifth example embodiments, the light guiding parts 4124 or 5124 can be formed such that the protrusion parts 4126 or 5126 are not located over the end of the sensor face 118 in a similar manner to the present example embodiment.

Seventh Example Embodiment

A fingerprint reading device and a fingerprint reading method according to a seventh example embodiment of the present invention will be described by using FIG. 21. Note that the same components as those in the fingerprint reading device and the fingerprint reading method according to the first to sixth example embodiments described above are labeled with the same references, and the description thereof will be omitted or simplified.

While a case where the edge part 128 and a part of the protrusion part 126 in the light guiding part 124 protrude and are located over the end of the sensor face 118 has been described in the first example embodiment described above, the light guiding part 124 is not necessarily required to be located over the end of the sensor face 118.

In the present example embodiment, a case where the light guiding part is not located over the end of the sensor face 118 will be described. Note that the fingerprint reading device according to the present example embodiment can be applied not only to a newborn or the like but also to an adult or the like as a subject whose fingerprint is read as with the fingerprint reading device 6010 according to the sixth example embodiment.

The basic configuration of the fingerprint reading device according to the present example embodiment is substantially the same as that of the fingerprint reading device 10 according to the first example embodiment. Since the fingerprint reading device according to the present example embodiment is different from the fingerprint reading device 10 according to the first example embodiment in the configuration of light guiding parts in the side light sources 112.

The specific configuration of the fingerprint reading device according to the present example embodiment will be described below by using FIG. 21. FIG. 21 is a transverse sectional view illustrating a fingerprint reading device according to the present example embodiment, which illustrates a horizontal cross section corresponding to the horizontal cross section of the fingerprint reading device 10 according to the first example embodiment illustrated in FIG. 4.

Figure 21:
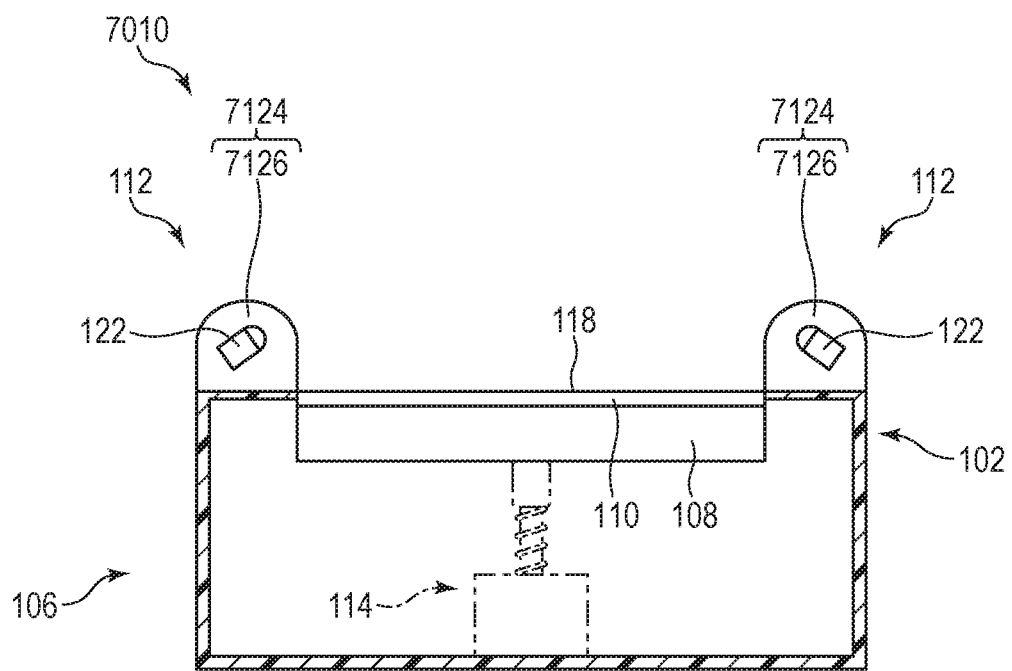
FIG. 21 is a transverse sectional view illustrating a fingerprint reading device according to a seventh example embodiment of the present invention.

As illustrated in FIG. 21, in a fingerprint reading device 7010 according to the present example embodiment, each of the pair of side light sources 112 has a light guiding part 7124 instead of the light guiding part 124 according to the first example embodiment. Note that the light-transmitting material of the light guiding parts 7124 is the same as that of the light guiding parts 124 according to the first example embodiment.

The light guiding part 7124 in each side light source 112 is formed extending in the front-rear direction of the placement portion 102 in a similar manner to the light guiding part 124 according to the first example embodiment. The light guiding part 7124 has a protrusion part 7126 only and does not have the skirt-like edge part 128.

The protrusion part 7126 is formed in a ridge-like manner so as to cover the plurality of near-infrared LEDs 122 and protrude above the placement portion 102 in a similar manner to the protrusion part 126 according to the first example embodiment. Unlike the protrusion part 126 according to the first example embodiment, however, the protrusion part 7126 is formed on the outer region of the sensor face 118 of the casing 106 so as to neither protrude over the end of the sensor face 118 nor be located over the end of the sensor face 118.

In the present example embodiment, unlike the first example embodiment, the skirt-like edge part 128 is not formed to the protrusion part 7126.

Further, in the present example embodiment, the light guiding part 7124 neither protrudes over the end of the sensor face 118 nor is located over the end of the sensor face 118. Thus, in the present example embodiment, unlike the first example embodiment, the light shielding part 130 is not provided to the light guiding part 7124.

As with the present example embodiment, the light guiding part 7124 may be formed of only the protrusion part 7126, and the light guiding part 7124 may not be located over the end of the sensor face 118.

Note that, while a case where the light guiding parts 7124 are provided instead of the light guiding parts 124 in the first example embodiment has been described above, the light guiding parts 7124 may be provided instead of the light guiding part 124 also in the second and third example embodiments.

Eighth Example Embodiment

Figure 22:
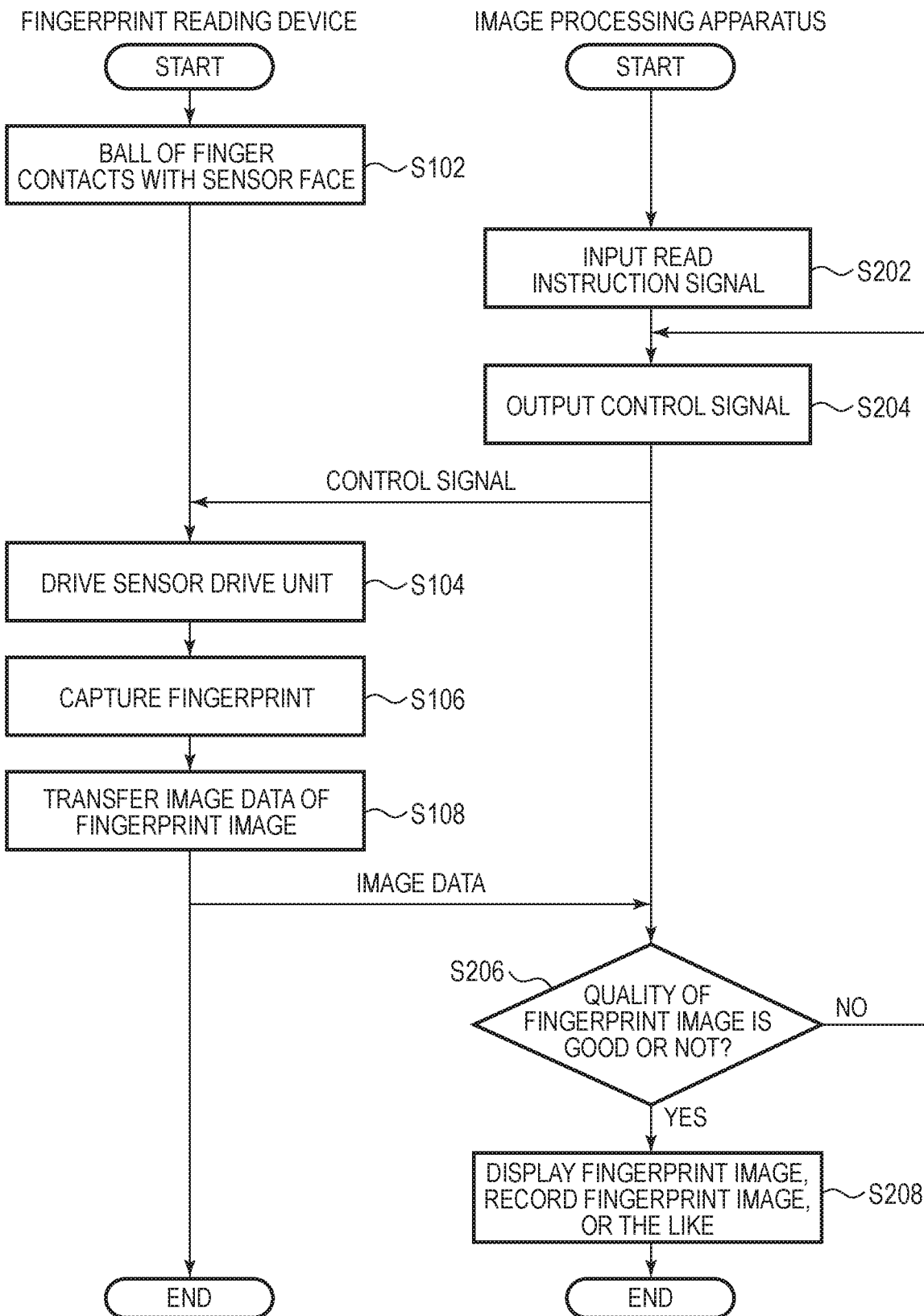
FIG. 22 is a flowchart illustrating the operation of a fingerprint reading device and an image processing apparatus according to an eighth example embodiment of the present invention.

A fingerprint reading device and a fingerprint reading method according to an eighth example embodiment of the present invention will be described by using FIG. 22. Note that the same components as those in the fingerprint reading device and the fingerprint reading method according to the first to seventh example embodiments described above are labeled with the same references, and the description thereof will be omitted or simplified.

While the case where a user or a subject presses the motion switch 142 and the capture switch 144 to have a fingerprint read has been described in the above first to seventh example embodiments, reading of a fingerprint can be automatically performed. In the present example embodiment, a case where reading of a fingerprint is automatically performed will be described in the first example embodiment.

In the present example embodiment, the image processing apparatus 20 in the fingerprint reading system 1 is configured to automate reading of a fingerprint performed by the fingerprint reading device 10. In the present example embodiment, the image processing apparatus 20 and the fingerprint reading device 10 are formed as described below.

In the image processing apparatus 20, the CPU 202 functions as a control unit that controls the operation of the fingerprint reading device 10 including the sensor drive unit 114 and the image sensor 108 and automates reading of a fingerprint performed by the fingerprint reading device 10. In response to a read instruction signal that is an instruction to read a fingerprint, the CPU 202 outputs a control signal used for controlling the fingerprint reading device 10 and inputs the control signal to the fingerprint reading device 10 via the communication cable 30. The control signal is a signal used for automating reading of a fingerprint performed by the fingerprint reading device 10. The control signal includes a drive instruction signal that is an instruction to drive the image sensor 108 and the sensor cover 110 and a capture instruction signal that is an instruction to capture a fingerprint after driving the image sensor 108 and the sensor cover 110.

The fingerprint reading device 10 and the image processing apparatus 20 can be configured such that, in response to the user pressing the capture switch 144, for example, the read instruction signal that is an instruction to read a fingerprint described above is input to the image processing apparatus 20 via the fingerprint reading device 10. Further, the image processing apparatus 20 may be configured such that, in response to the user operating the input device 218, the read instruction signal that is an instruction to read a fingerprint described above is input.

Furthermore, in the image processing apparatus 20, the CPU 202 functions as a determination unit that determines the quality of a fingerprint image transferred from the fingerprint reading device 10. The CPU 202 determines the quality of the fingerprint image transferred from the fingerprint reading device 10 based on a criterion regarding the fingerprint image quality. The CPU 202 determines that the quality of the fingerprint image is good if the quality of the fingerprint image is higher than or equal to a predetermined quality and determines that the quality of the fingerprint image is not good if the quality of the fingerprint image is lower than the predetermined quality.

If the CPU 202 determines that the quality of the fingerprint image is not good, the CPU 202 again outputs a control signal including a drive instruction signal and a capture instruction signal described above and inputs the control signal to the fingerprint reading device 10. In such a way, the CPU 202 functions as a control unit that controls the operation of the sensor drive unit 114 in accordance with the drive instruction signal based on the determination result on the quality of the fingerprint image and controls the operation of the image sensor 108 in accordance with the capture instruction signal.

On the other hand, in the fingerprint reading device 10, the CPU 166 drives the sensor drive unit 114 and the image sensor 108 based on the control signal input from the image processing apparatus 20. Specifically, the CPU 166 drives the sensor drive unit 114 in accordance with the drive instruction signal that is an instruction to drive the image sensor 108 and the sensor cover 110 included in the control signal. Thereby, the image sensor 108 and the sensor cover 110 including the sensor face 118 move from the capturing position to the recessed position and further move and return from the recessed position to the capturing position in the same manner as in the first example embodiment. Further, the CPU 166 causes the image sensor 108 to capture and read a fingerprint with the side light sources 112 being turned on in the same manner as in the first example embodiment in accordance with the capture instruction signal included in the control signal, which is an instruction to capture a fingerprint after driving the image sensor 108 and the sensor cover 110.

The operation of the fingerprint reading device 10 and the image processing apparatus 20 according to the present example embodiment will be described below by using FIG. 22. FIG. 22 is a flowchart illustrating the operation of the fingerprint reading device and the image processing apparatus according to the present example embodiment.

First, in the same manner as in the first example embodiment, the user causes the ball of a finger of a subject to come into contact with the sensor face 118 of the fingerprint reading device 10 in a state where the image sensor 108 and the sensor cover 110 including the sensor face 118 are positioned at the capturing position (step S102).

Next, the user inputs, to the image processing apparatus 20, a read instruction signal that is an instruction to read a fingerprint by using the input device 218, for example (step S202).

Next, the CPU 202 of the image processing apparatus 20 outputs a control signal that controls the fingerprint reading device 10 and inputs the control signal to the fingerprint reading device 10 in accordance with the read instruction signal input by the user (step S204). The control signal includes a drive instruction signal that is an instruction to drive the image sensor 108 and the sensor cover 110 and a capture instruction signal that is an instruction to capture a fingerprint after driving the image sensor 108 and the sensor cover 110. Note that, also in the present example embodiment, in the same manner as the configuration without the motion switch 142 being provided, the drive instruction signal and the capture instruction signal may be input to the fingerprint reading device 10 in the same manner as described above before the read instruction signal is input by the user in response to detection of contact the ball of the finger with the sensor face 118.

Next, the CPU 166 of the fingerprint reading device 10 drives the sensor drive unit 114 as described below based on the control signal input from the image processing apparatus 20 and then causes the image sensor 108 to capture a fingerprint (steps S104 and S106).

First, the CPU 166 drives the sensor drive unit 114 in accordance with the drive instruction signal included in the control signal input from the image processing apparatus 20 (step S104). Thereby, the image sensor 108 and the sensor cover 110 including the sensor face 118 move from the capturing position to the recessed position and further move and return from the recessed position to the capturing position in the same manner as in the first example embodiment. Note that, also in the present example embodiment, the same trigger as that in the first example embodiment can be used as a trigger by which the rear end part of the image sensor 108 and the sensor cover 110 is switched from moving down to moving up.

Next, the CPU 166 causes the image sensor 108 to capture and read a fingerprint with the side light source 112 being turned on in the same manner as in the first example embodiment in accordance with the capture instruction signal included in the control signal input from the image processing apparatus 20 (step S106).

In the same manner as in the first example embodiment, image data of the fingerprint image captured by the image sensor 108 is transferred to the image processing apparatus 20 via the communication cable 30 (step S108). In the same manner as in the first example embodiment, predetermined image processing is performed on the image data of the fingerprint image transferred to the image processing apparatus 20.

Next, the CPU 202 of the image processing apparatus 20 determines based on a criterion regarding the fingerprint image quality whether or not the quality of the fingerprint image transferred from the fingerprint reading device 10 is good (step S206).

If the CPU 202 determines that the quality of the fingerprint image is good (step S206, YES), the CPU 202 performs display, recording, or the like of the fingerprint image in the same manner as in the first example embodiment (step S208).

In contrast, if the CPU 202 determines that the quality of the fingerprint image is not good (step S206, NO), the CPU 202 proceeds to step S204, again outputs a control signal including a drive instruction signal and a capture instruction signal described above, and again inputs the control signal to the fingerprint reading device 10. Note that the CPU 202 may perform display or the like on the fingerprint image determined to be not good in the same manner as in the first example embodiment.

The CPU 166 of the fingerprint reading device 10 to which the control signal is again input from the image processing apparatus 20 again performs steps S104, S106, and S108. Thereby, the image data of the fingerprint image re-acquired in the fingerprint reading device 10 is again transferred to the image processing apparatus 20. By step S104 of driving the sensor drive unit 114 being executed again, reduction or removal of elastic deformation of a finger that is a factor of reduction in quality of a fingerprint image is attempted.

The CPU 202 of the image processing apparatus 20 to which the image data of the fingerprint image is again transferred executes step S206 again.

In such a way, reading of the fingerprint performed by the fingerprint reading device 10 is repeated until a fingerprint image having a quality of a predetermined value or higher is acquired.

As discussed above, in the present example embodiment, the image processing apparatus 20 controls the fingerprint reading device 10 to automatically read a fingerprint. Furthermore, in the present example embodiment, reading of a fingerprint performed by the fingerprint reading device 10 is repeated until a fingerprint image having a quality of a predetermined value or higher is acquired based on a result of the fingerprint image quality determined by the image processing apparatus 20. Therefore, according to the present example embodiment, a high quality fingerprint image can be efficiently acquired.

Further, while the case where the CPU 202 of the image processing apparatus 20 functions as the determination unit and the control unit that control the operation of the fingerprint reading device 10 to automate reading of a fingerprint performed by the fingerprint reading device 10 has been described above, the example embodiment is not limited thereto. For example, the CPU 166 of the control circuit 116 of the fingerprint reading device 10 may function as the whole or a part of the determination unit and the control unit that automate reading of a fingerprint performed by the fingerprint reading device 10 in a similar manner to the CPU 202 of the image processing apparatus 20 described above.

Further, while the case where reading of a fingerprint is automated in the first example embodiment has been described above, reading of a fingerprint can be automated in the second to seventh example embodiments in the same manner as described above.

Another Example Embodiment

Figure 23:
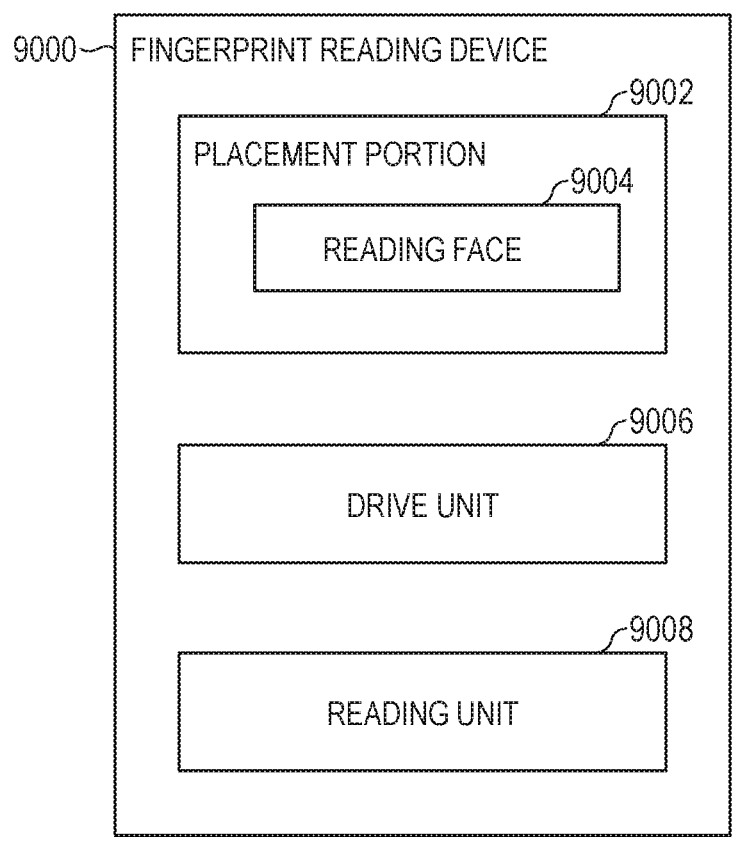
FIG. 23 is a block diagram illustrating a function configuration of a fingerprint reading device according to another example embodiment of the present invention.

According to another example embodiment, the fingerprint reading device described in each of the above example embodiments may be configured as illustrated in FIG. 23. FIG. 23 is a block diagram illustrating a function configuration of the fingerprint reading device according to another example embodiment.

As illustrated in FIG. 23, a fingerprint reading device 9000 according to another example embodiment has a placement portion 9002 on which a finger is placed. Further, the fingerprint reading device 900 has a reading face 9004 provided on the placement portion 9002 so as to be able to move between a first position where the finger placed on the placement portion 9002 comes into contact with the reading face 9004 and a second position where the finger placed on the placement portion 9002 separates from the reading face 9004. Further, the fingerprint reading device 9000 has a drive unit 9006 that causes the reading face 9004 to move between the first position and the second position. Furthermore, the fingerprint reading device 9000 has a reading unit 9008 that reads a fingerprint of the finger in contact with the reading face 9004 positioned at the first position. The drive unit 9006 causes the reading face 9004 in contact with the finger at the first position to move to the second position and further move from the second position to the first position. The reading unit 9008 reads a fingerprint of the finger in contact with the reading face 9004 that has moved from the second position to the first position.

According to the fingerprint reading device 9000 of another example embodiment, even when reading a fingerprint of a relatively soft finger that may be easily subjected to significant elastic deformation, it is possible to read the fingerprint appropriately.

Modified Example Embodiments

The present invention is not limited to the example embodiments described above, and various modifications are possible.

For example, while the case where the image sensor 108 that is a reading unit of an optical type that captures and reads a fingerprint is used has been described as an example in the above example embodiments, the reading unit is not limited thereto. As the reading unit that reads a fingerprint, various types such as an electrostatic capacitor type, an electric filed intensity type, or the like other than the optical type can be used.

Further, while the case where the image sensor 108 is driven by the sensor drive unit 114 together with the sensor cover 110 including the sensor face 118 with which a finger comes into contact has been described as an example in the above example embodiments, the invention is not limited thereto. Any configuration is possible as long as at least the sensor face 118 is driven as described in the example embodiments described above, and the image sensor 108 or other reading units that can read a fingerprint of a finger in contact with the sensor face 118 located in the capturing position may be fixed at a position separated from the sensor face 118.

The whole or part of the example embodiments disclosed above can be described as, but not limited to, the following supplementary notes.

(Supplementary Note 1)

A fingerprint reading device comprising:

a placement portion on which a finger is placed:

a reading face provided on the placement portion so as to be able to move between a first position where the finger placed on the placement portion comes into contact with the reading face and a second position where the finger placed on the placement portion separates from the reading face;

a drive unit that causes the reading face to move between the first position and the second position; and a reading unit that reads a fingerprint of the finger in contact with the reading face positioned at the first position, wherein the drive unit causes the reading face in contact with the finger at the first position to move to the second position and further move from the second position to the first position, and wherein the reading unit reads a fingerprint of the finger in contact with the reading face that has moved from the second position to the first position.

(Supplementary Note 2)

The fingerprint reading device according to supplementary note 1, wherein the drive unit causes the reading face to move between the first position and the second position by swinging or parallelly shifting the reading face.

(Supplementary Note 3)

The fingerprint reading device according to supplementary note 2, wherein the reading face is provided so as to be able to swing about a rocking shaft as a fulcrum that is located at a front end part of the placement portion and extends in a width direction of the placement portion, and wherein the drive unit causes the reading face to move between the first position and the second position by swinging the reading face.

(Supplementary Note 4)

The fingerprint reading device according to any one of supplementary notes 1 to 3 further comprising a pair of light sources provided on the placement portion and configured to irradiate the finger placed on the placement portion with lights, wherein the reading unit captures and reads the fingerprint by using lights scattered inside the finger and emitted from a surface of the finger.

(Supplementary Note 5)

The fingerprint reading device according to supplementary note 4, wherein the pair of light sources are inclined inward above the reading face positioned at the first position.

(Supplementary Note 6)

The fingerprint reading device according to supplementary note 4 or 5, wherein the pair of light sources are provided on both sides of ends of the reading face that are opposed in a width direction of the placement portion, and each of the pair of light sources has a light guiding part formed extending in a front-rear direction of the placement portion.

(Supplementary Note 7)

The fingerprint reading device according to supplementary note 6, wherein the light guiding part is formed to extend up to above the end of the reading face and configured to be able to support the finger placed on the placement portion.

(Supplementary Note 8)

The fingerprint reading device according to supplementary note 6 or 7, wherein each of the pair of light sources has a plurality of unit light sources arranged extending in the front-rear direction of the placement portion, and wherein the light guiding part is formed to cover the plurality of unit light sources.

(Supplementary Note 9)

The fingerprint reading device according to supplementary note 8, wherein the light guiding part has a protrusion part covering the plurality of unit light sources, and an edge part formed integrally with the protrusion part on the reading face side of the protrusion part and having a lower height in a perpendicular direction of the placement portion than the protrusion part.

(Supplementary Note 10)

The fingerprint reading device according to supplementary note 9, wherein the edge part and a part of the protrusion part are located over the end of the reading face.

(Supplementary Note 11)

The fingerprint reading device according to supplementary note 9, wherein a part of the edge part is located over the end of the reading face.

(Supplementary Note 12)

The fingerprint reading device according to any one of supplementary notes 9 to 11, wherein a width of the edge part located over the end of the reading face is wider toward a front side of the placement portion.

(Supplementary Note 13)

The fingerprint reading device according to any one of supplementary notes 9 to 11, wherein the edge part of the light guiding part for one of the pair of light sources and the edge part of the light guiding part for the other of the pair of light sources are formed to be continuous to each other above the reading face, and wherein an opening that exposes the reading face is formed in the edge parts.

(Supplementary Note 14)

The fingerprint reading device according to any one of supplementary notes 7 to 13 further comprising a light shielding part formed on an underside of the light guiding part in a portion located on the end of the reading face.

(Supplementary Note 15)

The fingerprint reading device according to any one of supplementary notes 1 to 14 further comprising:

a determination unit that determines a quality of a fingerprint image of the fingerprint read by the reading unit; and a control unit that controls an operation of the drive unit and the reading unit based on a determination result of the quality determined by the determination unit.

(Supplementary Note 16)

The fingerprint reading device according to any one of supplementary notes 1 to 15, wherein, in response to detection of contact of the finger with the reading face at the first position, the drive unit causes the reading face to move from the first position toward the second position.

(Supplementary Note 17)

The fingerprint reading device according to any one of supplementary notes 1 to 16, wherein, in response to detection of the finger separating from the reading face moving from the first position toward the second position, the drive unit causes the reading face to move toward the first position.

(Supplementary Note 18)

A fingerprint reading method of reading a fingerprint of a finger in contact with a reading face provided on a placement portion so as to be able to move between a first position where the finger placed on the placement portion comes into contact with the reading face and a second position where the finger placed on the placement portion separates from the reading face, the fingerprint reading method comprising:

placing the finger on the placement portion in which the reading face is positioned at the first position:

causing the reading face in contact with the finger at the first position to move to the second position and further move from the second position to the first position; and reading a fingerprint of the finger in contact with the reading face that has moved from the second position to the first position.

While the present invention has been described above with reference to the example embodiments, the present invention is not limited to the example embodiments described above. Various changes that can be appreciated by those skilled in the art within the scope of the present invention may be applied to the configuration or the detail of the present invention.

REFERENCE SIGNS LIST 1 fingerprint reading system
10, 2010, 3010, 4010, 5010, 6010, 7010, 9000 fingerprint reading device
20 image processing apparatus

What is claimed is:

1. A fingerprint reading device comprising:
a reading face;
an elastic member;
an image sensor;
a memory storing computer program instructions; and
a processor configured to:
control the elastic member to move the reading face between a first position and a second position in a direction that intersects a reading surface of the reading face; and
control the image sensor to read fingerprint information of a finger from the reading face which has moved from the second position to the first position after the reading face has moved from the first position to the second position.

2. The fingerprint reading device according to claim 1, wherein the elastic member causes the reading face to move between the first position and the second position by swinging or parallelly shifting the reading face.

3. The fingerprint reading device according to claim 2,
wherein the reading face is provided so as to be able to swing about a rocking shaft as a fulcrum that is located at a front end part of the reading face and extends in a width direction of the reading face, and
wherein the elastic member causes the reading face to move between the first position and the second position by swinging the reading face.

4. The fingerprint reading device according to claim 1 further comprising a pair of light sources provided on the reading face and configured to irradiate the finger placed on the reading face with lights,
wherein the image sensor captures and reads the fingerprint by using lights scattered inside the finger and emitted from a surface of the finger.

5. The fingerprint reading device according to claim 4, wherein the pair of light sources are inclined inward above the reading face positioned at the first position.

6. The fingerprint reading device according to claim 4, wherein the pair of light sources are provided on both sides of ends of the reading face that are opposed in a width direction of the reading face, and each of the pair of light sources has a light guiding part formed extending in a front-rear direction of the reading face.

7. The fingerprint reading device according to claim 6, wherein the light guiding part is formed to extend up to above the end of the reading face and configured to be able to support the finger placed on the reading face.

8. The fingerprint reading device according to claim 6,
wherein each of the pair of light sources has a plurality of unit light sources arranged extending in the front-rear direction of the reading face, and
wherein the light guiding part is formed to cover the plurality of unit light sources.

9. The fingerprint reading device according to claim 8, wherein the light guiding part has
a protrusion part covering the plurality of unit light sources, and
an edge part formed integrally with the protrusion part on the reading face side of the protrusion part and having a lower height in a perpendicular direction of the reading face than the protrusion part.

10. The fingerprint reading device according to claim 9, wherein the edge part and a part of the protrusion part are located over the end of the reading face.

11. The fingerprint reading device according to claim 9, wherein a part of the edge part is located over the end of the reading face.

12. The fingerprint reading device according to claim 9, wherein a width of a portion of the edge part located over the end of the reading face is wider toward a front side of the reading face.

13. The fingerprint reading device according to claim 9,
wherein the edge part of the light guiding part for one of the pair of light sources and the edge part of the light guiding part for the other of the pair of light sources are formed to be continuous to each other above the reading face, and
wherein an opening that exposes the reading face is formed in the edge parts.

14. The fingerprint reading device according to claim 7 further comprising a light shielding part formed on an underside of the light guiding part in a portion located on the end of the reading face.

15. The fingerprint reading device according to claim 1, wherein the processor is further configured to:
determine a quality of a fingerprint image of the fingerprint read by the image sensor; and control an operation of the elastic member and the image sensor based on the determined quality.

16. The fingerprint reading device according to claim 1, wherein, in response to detection of contact of the finger with the reading face at the first position, the elastic member causes the reading face to move from the first position toward the second position.

17. The fingerprint reading device according to claim 1, wherein, in response to detection of the finger separating from the reading face moving from the first position toward the second position, the elastic member causes the reading face to move toward the first position.

18. The fingerprint reading device according to claim 1, further comprising a drive unit comprising the elastic member.

19. The fingerprint reading device according to claim 18, wherein the drive unit is manually operable.

20. A fingerprint reading method of reading a fingerprint of a finger in contact with a reading face so as to be able to move between a first position and a second position, the fingerprint reading method comprising:
- placing the finger on the reading face in which the reading face is positioned at the first position;
- causing the reading face to move to the second position and further move from the second position to the first position in a direction that intersects a reading surface of the reading face; and
- reading fingerprint information of the finger from the reading face which has moved from the second position to the first position after the reading face has moved from the first position to the second position.

\* \* \* \* \*